(12) United States Patent
Valencia et al.

(10) Patent No.: US 9,931,410 B2
(45) Date of Patent: Apr. 3, 2018

(54) NANOPARTICLES FOR TARGETED DELIVERY OF MULTIPLE THERAPEUTIC AGENTS AND METHODS OF USE

(71) Applicants: The Brigham and Women's Hospital, Inc., Boston, MA (US); Massachusetts Institute of Technology, Cambridge, MA (US)

(72) Inventors: Pedro M. Valencia, Cambridge, MA (US); Eric M. Pridgen, Boston, MA (US); Suresh Gadde, Brookline, MA (US); Rohit Karnik, Cambridge, MA (US); Robert S. Langer, Newton, MA (US); Stephen J. Lippard, Cambridge, MA (US); Omid C. Farokhzad, Waban, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/434,300

(22) PCT Filed: Oct. 9, 2013

(86) PCT No.: PCT/US2013/064138
§ 371 (c)(1),
(2) Date: Apr. 8, 2015

(87) PCT Pub. No.: WO2014/059022
PCT Pub. Date: Apr. 17, 2014

(65) Prior Publication Data
US 2015/0265716 A1    Sep. 24, 2015

Related U.S. Application Data

(60) Provisional application No. 61/711,655, filed on Oct. 9, 2012.

(51) Int. Cl.
| | | |
|---|---|---|
| *A61K 47/48* | (2006.01) | |
| *A61K 45/06* | (2006.01) | |
| *A61K 31/555* | (2006.01) | |
| *A61K 33/24* | (2006.01) | |
| *A61K 9/14* | (2006.01) | |
| *A61K 9/51* | (2006.01) | |
| *A61K 31/4745* | (2006.01) | |
| *A61K 47/34* | (2017.01) | |
| *A61K 47/59* | (2017.01) | |
| *A61K 47/68* | (2017.01) | |
| *A61K 47/69* | (2017.01) | |
| *B82Y 5/00* | (2011.01) | |

(52) U.S. Cl.
CPC .............. *A61K 47/482* (2013.01); *A61K 9/14* (2013.01); *A61K 9/51* (2013.01); *A61K 9/5146* (2013.01); *A61K 31/4745* (2013.01); *A61K 31/555* (2013.01); *A61K 33/24* (2013.01); *A61K 45/06* (2013.01); *A61K 47/34* (2013.01); *A61K 47/593* (2017.08); *A61K 47/6869* (2017.08); *A61K 47/6937* (2017.08); *A61K 9/5153* (2013.01); *B82Y 5/00* (2013.01)

(58) Field of Classification Search
CPC .... A61K 47/482; A61K 45/06; A61K 31/555; A61K 33/24; A61K 9/14; A61K 9/51; A61K 9/5146; A61K 31/4745; A61K 47/34; A61K 47/593; A61K 47/6869; A61K 47/6937; A61K 9/5153; B82Y 5/00
See application file for complete search history.

(56) References Cited

U.S. PATENT DOCUMENTS

| | | | | |
|---|---|---|---|---|
| 2003/0147945 | A1* | 8/2003 | Tardi ................... | A61K 9/127 424/450 |
| 2004/0091546 | A1 | 5/2004 | Johnson et al. | |
| 2008/0248126 | A1 | 10/2008 | Cheng et al. | |
| 2008/0299205 | A1* | 12/2008 | Mayer ................... | A61K 8/85 424/489 |

(Continued)

FOREIGN PATENT DOCUMENTS

| | | |
|---|---|---|
| WO | 05/058376 | 6/2005 |
| WO | WO 2007/150030 | 12/2007 |

(Continued)

OTHER PUBLICATIONS

Chris Oerlemans, et al, Polymeric Micelles in Anticancer Therapy: Targeting, Imaging and Triggered Release, 27 Pharm. Res. 2569 (2010).*

Chabner et al., "Chemotherapy and the war on cancer," Nat. Rev. Cancer, Jan. 2005, 5:65-72.

Chandran et al., "Characterization of a targeted nanoparticle functionalized with a urea-based inhibitor of prostate-specific membrane antigen (PSMA)," Cancer Biol. Ther., Jul. 1, 2008, 7:974-982.

Chou et al., Pharmacol. Rev., Theoretical basis, experimental design, and computerized simulation of synergism and antagonism in drug combination studies, Sep. 2006, 58(3):621-681.

Cotten et al., "Receptor-mediated transport of DNA into eukaryotic cells," Methods Enzym., 1993, 217:618-644.

DeMello and DeMello, "Microscale reactors: nanoscale products," Lab on a Chip, Apr. 2004, 4(2):11N-15N.

Fredenberg et al., "The mechanisms of drug release in poly(lactic-co-glycolic acid)-based drug delivery systems—a review," Int. J. Pharmaceut., Aug. 30, 2011, 415:34-52.

(Continued)

*Primary Examiner* — Sean M Basquill
(74) *Attorney, Agent, or Firm* — Fish & Richardson P.C.

(57) ABSTRACT

Provided herein are compositions that contain a nanoparticle containing a plurality of polymers, wherein at least a fraction of the polymers comprise a hydrophobic polymer, a topoisomerase inhibitor, and a Pt-containing chemotherapeutic agent, where the polymers self-assemble in an aqueous liquid to form the nanoparticle, and where the Pt-containing chemotherapeutic agent and the topoisomerase inhibitor are present within the hydrophobic core of the nanoparticle in a ratio of between about 24:1 to about 1:24. Also provided are methods of reducing the proliferation of a cancer cell and methods of treating cancer in a subject that include the use of these compositions. Also provided are methods of making these nanoparticles.

23 Claims, 10 Drawing Sheets

(56) References Cited

U.S. PATENT DOCUMENTS

2009/0061010 A1* 3/2009 Zale ............... A61K 9/5153
424/501
2009/0105172 A1 4/2009 Diener et al.

FOREIGN PATENT DOCUMENTS

| WO | WO 2008/124632 | 10/2008 |
| WO | WO 2011/084620 | 7/2011 |

OTHER PUBLICATIONS

Garnett, "Targeted drug conjugates: principles and progress," Adv. Drug Deliv. Rev., Dec. 2001, 53:171-216.
Gerhardt et al., "Functional Lactide Monomers: Methodology and Polymerization," Biomacromolecules, Jun. 2006, 7(6):1735-1742.
Ghosh and Heston, "Tumor target prostate specific membrane antigen (PSMA) and its regulation in prostate cancer," J. Cell. Biochem., Feb. 2004, 91:528-539.
Hamidi et al., "Pharmacokinetic Consequences of Pegylation," Drug Deliv., 2006, 13:399-409.
International Preliminary Report on Patentability in International Application No. PCT/US2013/064138, dated Apr. 14, 2015, 15 pages.
Javier et al., "Aptamer-Targeted Gold Nanoparticles As Molecular-Specific Contrast Agents for Reflectance Imaging," Bioconjug. Chem., 2008, 19(6):1309-1312.
Jiang et al. "Clickable Polyglycolides: Tunable Synthons for Thermoresponsive, Degradable Polymers," Macromolecules, 2008, 41(6):1937-44.
Jing et al., "A bifunctional monomer derived from lactide for toughening polylactide," J. Am. Chem. Soc., Oct. 22, 2008, 130(42):13826-27.
Johnson et al., "Mechanism for Rapid Self-Assembly of Block Copolymer Nanoparticles," Phys. Rev. Lett., Sep. 2003 91:118302.
Karnik et al., "Microfluidic Platform for Controlled Synthesis of Polymeric Nanoparticles," Nano Lett., Sep. 2008, 8(9):2906-2912.
Karnik et al., "Single-step assembly of homogenous lipid-polymeric and lipid-quantum dot nanoparticles enabled by microfluidic rapid mixing," ACS Nano, Mar. 23, 2010, 4(3):1671-1679.
Kimura et al., "Ring-Opening Polymerization of 3(S)-[(Benzyloxycarbonyl)methyl]-1,4-dioxane-2,5-dione: A New Route to a Poly(a-hydroxy acid) with Pendant Carboxyl Groups," Macromolecules, 1988, 21(11):3338-40.
Kolishetti et al., "Engineering of self-assembled nanoparticle platform for precisely controlled combination drug therapy," Proc. Natl. Acad. Sci. U.S.A., Oct. 2010, 107(42):17939-17944.
Langer and Tirrell, "Designing materials for biology and medicine," Nature, Apr. 1, 2004, 428:487- 492.
Leemhuis et al., "In Vitro Hydrolytic Degradation of Hydroxyl-Functionalized Poly($\alpha$-hydroxy acid)s," Biomacromolecules, Aug. 23, 2007, 8(9):2943-2949.
Leemhuis et al., "A Versatile Route to Functionalized Dilactones as Monomers for the Synthesis of Poly($\alpha$-hydroxy) Acids," Eur. J. Org. Chem, 2003, 3344-3449.
Leemhuis et al., "Functionalized Poly(R-hydroxy acid)s via Ring-Opening Polymerization: Toward Hydrophilic Polyesters with Pendant Hydroxyl Groups," Macromolecules, 2006, 39:3500-3508.
Liu et al., "Marine bromophenol bis (2,3-dibromo-4,5-dihydroxybenzyl) ether, induces itochondrial apoptosis in K562 cells and inhibits topoisomerase I in vitro," Toxicol. Lett., Jun. 1, 2012, 211(2):126-134.
Milowsky et al., "Vascular Targeted Therapy With Anti-Prostate-Specific Membrane Antigen Monoclonal Antibody J591 in Advanced Solid Tumors," J. Clin. Oncol., Feb. 10, 2007, 25(5):540-547.
Morris et al., "Phase I evaluation of J591 as a vascular targeting agent in progressive solid tumors," Clin. Cancer Res., May 1, 2007, 13(9):2707-2713.
Gen Bank Accession No. AAA61207.1, "topoisomerase I [*Homo sapiens*]," dated Jan. 14, 1995, retrieved on Jun. 20, 2016, http://www.ncbi.nlm.nih.gov/protein/339806.
Gen Bank Accession No. CAA48197.1, "DNA topoisomerase II [*Homo sapiens*]," dated Oct. 21, 2008, retrieved on Jun. 20, 2016, http://www.ncbi.nlm.nih.gov/protein/37231.
Nguyen et al., "Micromixers—a review," J. Micromechan. Microeng., 2005, 15:R1-R16.
Noga et al., "Synthesis and Modification of Functional Poly(lactide) Copolymers: Toward Biofunctional Materials," Biomacromolecules, 2008, 9:2056-2062.
Pasqualini et al., "Searching for a molecular address in the brain," Mol. Psychiatry, Dec. 1996, 1(6):421-2.
Rajotte et al., "Molecular heterogeneity of the vascular endothelium revealed by in vivo phage display," J. Clin. Invest., Jul. 1998, 102:430-437.
Rhee et al., "Synthesis of Size-Tunable Polymeric Nanoparticles Enabled by 3D Hydrodynamic Flow Focusing in Single-Layer Microchannels," Adv. Mater., Mar. 25, 2011, 23(12):H79-H83.
Tardi et al., "Drug ratio-dependent antitumor activity of irinotecan and cisplatin combinations in vitro and in vivo," Mol Cancer Ther., 2009, 8(8):2266-2275.
Torchilin, "Drug Targeting," Eur. J. Pharm. Sci., 2000, 11:S81-S91.
Trimaille et al., "Synthesis and Properties of Novel Poly(Hexyl-Substituted Lactides) for Pharmaceutical Applications," Chimia, Jun. 2005, 59(6):348-352.
Trimaille et al., "Poly(hexyl-substituted lactides): Novel injectable hydrophobic drug delivery systems," J. Biomed. Mater. Res., Jan. 2007, 80A(1):55-65.
Valencia et al., "Single-Step Assembly of Homogenous Lipid—Polymeric and Lipid—Quantum Dot Nanoparticles Enabled by Microfluidic Rapid Mixing," ACS Nano, Mar. 23, 2010, 4(3):1671-1679.
Vauthier et al., "Measurement of the Density of Polymeric Nanoparticulate Drug Carriers by Isopycnic Centrifugation," J. Nanoparticles Res., Sep. 1999, 1(3):411-418.
Veronese et al., "The Impact of PEGylation on Biological Therapies," BioDrugs, Sep. 2008, 22:315-329.
Yalowich et al., "The anticancer thiosemicarbazones Dp44mT and triapine lack inhibitory effects as catalytic inhibitors or poisons of DNA topoisomerase II$\alpha$," Biochem. Pharmacol., Jul. 2012, 84(1):52-58.
Zastre et al., "Irinotecan—cisplatin interactions assessed in cell-based screening assays: cytotoxicity, drug accumulation and DNA adduct formation in an NSCLC cell line," Cancer Chemother. Pharmacol., Jun. 2007, 60(1):91-102.
Oerlemans et al., "Polymeric Micelles in Anticancer Therapy: Targeting, Imaging and Triggered Release," Pharm. Res., 2010, 27, pp. 2569-2589.
Tatsuya Nagano et al., "Antitumor Activity of NK012 Combined with Cisplatin against Small Cell Lung Cancer and Intestinal Mucosal Changes in Tumor-Bearing Mouse after Treatment," Clin. Cancer Res., 2009, 15(13), pp. 4348-4355.
Hrkach et al., "Preclinical Development and Clinical Translation of a PSMATargeted Docetaxel Nanoparticle with a Differentiated Pharmacological Profile," Sci. Transl. Med., Apr. 4, 2012, vol. 4, Issue 128, 128ra39.
International Serach Report and Written Opinion of the International Searching Authority dated Dec. 26, 2013 for International Application No. PCT/US2013/064138, 8 pgs.

* cited by examiner

| Combination Index (CI)** | |
|---|---|
| Antagonism (worse than additive) | >1 |
| Additive effect | ~1 |
| Synergism (better than additive) | <1 |
| Irinotecan-Cisplatin NPs | 0.20 |

NANOPARTICLES FOR TARGETED DELIVERY OF MULTIPLE THERAPEUTIC AGENTS AND METHODS OF USE

CROSS-REFERENCE TO RELATED APPLICATIONS

This application is a U.S. National Phase Application under 35 U.S.C. § 371 of International Patent Application No. PCT/US2013/064138, filed on Oct. 9, 2013, which claims the benefit of U.S. Provisional Patent Application No. 61/711,655, filed on Oct. 9, 2012. The contents of the foregoing applications are incorporated herein by reference in their entirety.

FEDERALLY SPONSORED RESEARCH DEVELOPMENT

This invention was made with Government support under Grant Number EB003647 awarded by the National Institutes of Health. The Government has certain rights in this invention.

TECHNICAL FIELD

This invention relates to the field of cancer biology and medicine.

BACKGROUND OF THE INVENTION

Combination chemotherapy has been used to treat diverse types of cancer (Chabner et al., Nat. Rev. Cancer 5:65-72, 2005). While drug combination is an option for cancer therapy, the reality is that combination chemotherapies have several disadvantages, including (1) distinct pharmacokinetics and tissue distribution of each drug due to differences in each drug's physicochemical properties, and (2) more serious side effects, because each drug may have different toxicity profiles. These disadvantages make dosing and scheduling of each drug a challenging task.

SUMMARY

The inventions described herein are based, at least in part, on the discovery that targeted and non-targeted nanoparticles that contain both a Pt-containing chemotherapeutic drug and a topoisomerase inhibitor result in a significant improvement in inhibiting or reducing cancer cell proliferation. In view of this discovery, the present disclosure provides compositions that contain nanoparticles (targeted and non-targeted nanoparticles) containing: a plurality of polymers, where at least a fraction of the polymers contain a hydrophobic polymer linked to a platinum (Pt)-containing chemotherapeutic agent, and a topoisomerase inhibitor, where the polymers self-assemble in an aqueous liquid to form the nanoparticle, and where the Pt-containing chemotherapeutic agent and the topoisomerase inhibitor are present within the hydrophobic core of the nanoparticle in a ratio of between about 24:1 to about 1:24 (e.g., about 15:1 to about 1:15, about 10:1 to about 1:10, about 5:1 to about 1:5, about 4:1 to about 1:4, or about 2:1 to about 1:2. The nanoparticles can be targeted and contain a targeting moiety linked to at least one of the polymers, where the targeting moiety is exposed on an outer surface of the nanoparticle (e.g., present on the outer surface of the nanoparticle at a density of about 500 to about 1,000,000 molecules per $\mu m^2$). In some embodiments, the topoisomerase inhibitor is linked to at least one of the polymers.

Also provided are compositions containing a nanoparticle (e.g., targeted and non-targeted) containing a plurality of polymers, where at least a fraction of the polymers contain a hydrophobic polymer linked to a topoisomerase inhibitor, and a platinum-containing chemotherapeutic agent, where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio of between about 24:1 to about 1:24 (e.g., about 15:1 to about 1:15, about 10:1 to about 1:10, about 5:1 to about 1:5, about 4:1 to about 1:4, or about 2:1 to about 1:2).

Also provided are compositions containing a nanoparticle containing a plurality of polymers, where at least a fraction of the polymers contain a hydrophobic polymer, a platinum-containing chemotherapeutic agent, and a topoisomerase inhibitor, where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio between about 24:1 to about 1:24 (e.g., about 15:1 to about 1:15, about 10:1 to about 1:10, about 5:1 to about 1:5, about 4:1 to about 1:4, or about 2:1 to about 1:2).

Also provided are methods of reducing the proliferation of a cancer cell and methods of treating cancer in a subject that include the use of these compositions, and methods of making these targeted nanoparticles.

Provided herein are compositions containing a nanoparticle containing: a plurality of polymers, wherein at least a fraction of the polymers comprise a hydrophobic polymer linked to a platinum (Pt)-containing chemotherapeutic agent; and a topoisomerase inhibitor; where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio between about 1:4 to about 4:1. Some embodiments further contain a targeting moiety linked to at least one of the polymers, where the targeting moiety is exposed on an outer surface of the nanoparticle. In some embodiments of any of the compositions described herein, the topoisomerase inhibitor is linked to at least one of the polymers. In some embodiments of any of the compositions described herein, the targeting moiety specifically binds to prostate-specific membrane antigen. In some embodiments of any of the compositions described herein, the targeting moiety is a nucleic acid, a small molecule, or a polypeptide. In some embodiments, the nucleic acid comprises at least one nucleoside analogue or at least one modification in a polyphosphate backbone. In some embodiments, the nucleic acid is an aptamer. In some embodiments, the small molecule is a carbohydrate or hydrocarbon. In some embodiments, the small molecule is S,S-2[3-][5-amino-1-carboxypentyl]-ureido]-pentanedioic acid (LIG). In some embodiments, the polypeptide is selected from the group of: a growth factor, a hormone, a cytokine, an interleukin, an antibody, an antigen-binding antibody fragment, an integrin, a fibronectin receptor, a P-glycoprotein receptor, a peptidomimetic, an affibody, a nanobody, an avimer, a small modular immunopharmaceutical, and an adnectin, or a fragment thereof. In some embodiments, the targeting moiety is linked to at least one of the polymers through an ester, an amide, or an ether bond.

Some embodiments of any of the compositions described herein further contain comprising a pharmaceutically acceptable excipient. In some embodiments of any of the compositions described herein, the plurality of polymers includes at least one amphiphilic polymer. In some embodiments, the at least one amphiphilic polymer contains poly (lactide-co-glycolic acid)-polyethylene glycol (PLGA-PEG) or polylactic acid (PLA)-PEG. In some embodiments, the plurality of polymers includes (i) at least one amphiphilic polymer containing at least one first hydrophobic polymer and at least one hydrophilic polymer, and (ii) at least one second hydrophobic polymer that self-assemble in an aqueous liquid to form the nanoparticle, and where the at least one first hydrophobic polymer and the at least one second hydrophobic polymer form a hydrophobic core of the nanoparticle, and the at least one hydrophilic polymer forms a shell of the nanoparticle. In some embodiments of any of the compositions described herein, the hydrophobic polymer contains a polycaprolactone, a polyanhydride, a polyalkylene, a polycarbonate, a polyhydroxyacid, a polyfumarate, a polycaprolactone, a polyamide, a polyacetal, a polyether, a polyester, a poly(orthoester), a polyvinyl alcohol, a polyurethane, a polyphosphazene, a polyacrylate, a polymethacrylate, a polycyanoacrylate, a polyurea, a polystyrene, or a polyamine. In some embodiments, the polyester is a polylactic acid.

In some embodiments of any of the compositions described herein, the Pt-containing chemotherapeutic agent is selected from the group of: cisplatin, carboplatin, oxaliplatin, satraplatin, picoplatin, and aroplatin. In some embodiments of any of the compositions described herein the Pt-containing chemotherapeutic agent is cisplatin. In some embodiments of any of the compositions described herein, the Pt-containing chemotherapeutic agent is linked to the hydrophobic polymer through an ester, an amide, or an ether bond. In some embodiments of any of the compositions described herein, the topoisomerase inhibitor is selected from the group consisting of: irinotecan, SN-38, topotecan, camptothecin, and lamellarin D. In some embodiments of any of the compositions described herein, the topoisomerase inhibitor is irinotecan. In some embodiments of any of the compositions described herein, the nanoparticle further comprises an outer layer comprising a surfactant.

In some embodiments, the plurality of polymers contains poly(lactide-co-glycolic acid)-polyethylene glycol (PLGA-PEG) and polylactic acid; the targeting moiety is S,S-2[3-][5-amino-1-carboxypentyl]-ureido]-pentanedioic acid (LIG); the Pt-containing chemotherapeutic agent is cisplatin; and the topoisomerase inhibitor is irinotecan. In some embodiments of all of the compositions described herein, the topoisomerase inhibitor and Pt-containing chemotherapeutic agent are present in a ratio of about 3:1 to 4:1.

In some embodiments of any of the compositions described herein, the nanoparticle has a diameter of about 40 nm to 80 nm (e.g., about 45 nm to 65 nm). In some embodiments of any of the compositions described herein, the composition is formulated for intravenous, intraarterial, intraperitoneal, subcutaneous, intrathecal, ocular, or intramuscular administration. Some embodiments of any of the compositions described herein further contain one or more additional anti-cancer agents selected from the group of: an alkylating agent, an antimetabolite, an anthracycline, a plant alkyloid, and a therapeutic antibody or antigen-binding antibody fragment that specifically binds to a tumor antigen. Also provided are pharmaceutical compositions that contain one or more of any of the compositions described herein.

Also provided are methods of reducing the proliferation of a cancer cell that include contacting a cancer cell with any of the compositions described herein in an amount sufficient to reduce the proliferation of the cancer cell. In some embodiments, the proliferation of the cancer cell is reduced by at least 10% within 24 hours of contact with the composition. In some embodiments, the cancer cell is present in vitro. In some embodiments, the cancer cell is present in a mammal. In some embodiments, the mammal has been previously diagnosed as having a cancer. In some embodiments of any of the methods described herein, the cancer is selected from the group of: breast cancer, colon cancer, leukemia, bone cancer, lung cancer, bladder cancer, brain cancer, bronchial cancer, cervical cancer, colorectal cancer, endometrial cancer, ependymoma, retinoblastoma, gallbladder cancer, gastric cancer, gastrointestinal cancer, glioma, head and neck cancer, heart cancer, liver cancer, pancreatic cancer, melanoma, kidney cancer, laryngeal cancer, lip or oral cancer, lymphoma, mesothioma, mouth cancer, myeloma, nasopharyngeal cancer, neuroblastoma, oropharyngeal cancer, ovarian cancer, thyroid cancer, penile cancer, pituitary cancer, prostate cancer, rectal cancer, renal cancer, salivary gland cancer, sarcoma, skin cancer, stomach cancer, testicular cancer, throat cancer, uterine cancer, vaginal cancer, and vulvar cancer.

In some embodiments, the contacting results in treatment of cancer in the mammal. In some embodiments of any of the methods described herein, the mammal is a human. In some embodiments, the composition is administered by intravenous, intraarterial, subcutaneous, intraperitoneal, intramuscular, ocular, or intrathecal administration. In some embodiments of any of the methods described herein, the cancer cell is selected from the group of: a breast cancer cell, a colon cancer cell, a leukemia cell, a bone cancer cell, a lung cancer cell, a bladder cancer cell, a brain cancer cell, a bronchial cancer cell, a cervical cancer cell, a colorectal cancer cell, an endometrial cancer cell, an ependymoma cancer cell, a retinoblastoma cancer cell, a gallbladder cancer cell, a gastric cancer cell, a gastrointestinal cancer cell, a glioma cancer cell, a head and neck cancer cell, a heart cancer cell, a liver cancer cell, a pancreatic cancer cell, a melanoma cancer cell, a kidney cancer cell, a laryngeal cancer cell, a lip or oral cancer cell, a lymphoma cancer cell, a mesothioma cancer cell, a mouth cancer cell, a myeloma cancer cell, a nasopharyngeal cancer cell, a neuroblastoma cancer cell, an oropharyngeal cancer cell, an ovarian cancer cell, a thyroid cancer cell, a penile cancer cell a pituitary cancer cell, a prostate cancer cell, a rectal cancer cell, a renal cancer cell, a salivary gland cancer cell, a sarcoma cancer cell, a skin cancer cell, a stomach cancer cell, a testicular cancer cell, a throat cancer cell, a uterine cancer cell, a vaginal cancer cell, and a vulvar cancer cell. Some embodiments of any of the methods described herein further include contacting the cancer cell with one or more additional anti-cancer agents selected from the group of: an alkylating agent, an antimetabolite, an anthracycline, a plant alkyloid, and a therapeutic antibody or an antigen-binding antibody fragment that specifically binds to a tumor antigen.

In some embodiments of any of the methods described herein, the plurality of polymers contain poly (lactide-co-glycolic acid)-polyethylene glycol (PLGA-PEG) and polylactic acid; the Pt-containing chemotherapeutic agent is cisplatin; the topoisomerase inhibitor is irinotecan; and the nanoparticle further contains a targeting moiety of S,S-2[3-][5-amino-1-carboxypentyl]-ureido]-pentanedioic acid (LIG) linked to at least one of the polymers, and the targeting moiety is exposed on an outer surface of the nanoparticle. In some embodiments of any of the methods described herein, the nanoparticle in the composition contains irinotecan and cisplatin in a ratio of about 3:1 to 4:1.

Also provided are methods of making a nanoparticle that include: mixing (i) a plurality of polymers, where at least a fraction of the polymers contain a hydrophobic polymer linked to a platinum (Pt)-containing chemotherapeutic agent; and (ii) a topoisomerase inhibitor in an organic solvent to form an organic precursor solution; and contacting the organic precursor solution with an aqueous solvent to achieve a ratio of 5:1 to 20:1 volume of organic precursor solution to volume of aqueous solvent, where the contacting results in the self-assembly of a nanoparticle. In some embodiments, the plurality of polymers further comprises at least one polymer linked to a targeting moiety. In some embodiments of any of these methods, the topoisomerase inhibitor is linked to at least one of the polymers. In some embodiments of any of these methods, the organic solvent contains acetonitrile.

In some embodiments of any of these methods, the contacting is performed by passing the organic precursor solution through a microfluidic device. In some embodiments, the passing of the organic precursor solution through the microfluidic device is performed at a rate of between 1 µL/minute to 100 µL/minute. In some embodiments of any of these methods, the plurality of polymers contains an amphiphilic polymer and a hydrophobic polymer in a ratio of approximately 3:1. In some embodiments of any of these methods, the the nanoparticle has a diameter of between 40 nm to 80 nm. In some embodiments of any of these methods, the plurality of polymers contains a poly(lactide-co-glycolic acid) polyethylene glycol (PLGA-PEG) or polylactic acid (PLA)-PEG. In some embodiments of any of these methods, the targeting moiety specifically binds to prostate-specific membrane antigen. In some embodiments, the targeting moiety is a nucleic acid, a small molecule, or a polypeptide. In some embodiments, the nucleic acid contains at least one nucleoside analogue or at least one modification in the polyphosphate backbone. In some embodiments, the nucleic acid is an aptamer. In some embodiments, the small molecule is a carbohydrate or hydrocarbon. In some embodiments, the small molecule is S,S-2[3-][5-amino-1-carboxypentyl]-ureido]-pentanedioic acid (LIG). In some embodiments, the polypeptide is selected from the group of: a growth factor, a hormone, a cytokine, an interleukin, an antibody, an antigen-binding antibody fragment, an integrin, a fibronectin receptor, a P-glycoprotein receptor, a peptidomimetic, an affibody, a nanobody, an avimer, a small modular immunopharmaceutical and an adnectin, or a fragment thereof. In some embodiments of any of these methods, the targeting moiety is linked to at least one of the polymers through an ester, an amide, or an ether bond.

In some embodiments of any of these methods, the fraction of the polymers containing a hydrophobic polymer comprise a polycaprolactone, a polyanhydride, a polyalkylene, a polycarbonate, a polyhydroxyacid, a polyfumarate, a polycaprolactone, a polyamide, a polyacetal, a polyether, a polyester, a poly(orthoester), a polyvinyl alcohol, a polyurethane, a polyphosphazene, a polyacrylate, a polymethacrylate, a polycyanoacrylate, a polyurea, a polystyrene, or a polyamine. In some embodiments, the polyester is a polylactic acid. In some embodiments of any of these methods, the Pt-containing chemotherapeutic agent is selected from the group of: cisplatin, carboplatin, oxaliplatin, satraplatin, picoplatin, and aroplatin. In some embodiments of any of these methods, the Pt-containing chemotherapeutic agent is cisplatin. In some embodiments of any of these methods, the Pt-containing chemotherapeutic agent is linked to the hydrophobic polymer through an ester, an amide, or an ether bond. In some embodiments of any of these methods, the topoisomerase inhibitor is selected from the group of: irinotecan, SN-38, topotecan, camptothecin, and lamellarin D. In some embodiments of any of these methods, the topoisomerase inhibitor is irinotecan. In some embodiments of these methods, the plurality of copolymers contains poly (lactide-co-glycolic acid) polyethylene glycol (PLGA-PEG) and polylactic acid (PLA); the targeting moiety is S,S-2[3-][5-amino-1-carboxypentyl]-ureido]-pentanedioic acid (LIG); the Pt-containing chemotherapeutic agent is cisplatin; and the topoisomerase inhibitor is irinotecan. In some embodiments of any of these methods, the nanoparticle contains the topoisomerase inhibitor and the Pt-containing chemotherapeutic agent in a ratio of about 3:1 to about 4:1.

Also provided are compositions containing a nanoparticle containing a plurality of polymers, where at least a fraction of the polymers contain a hydrophobic polymer linked to a topoisomerase inhibitor; and a platinum-containing chemotherapeutic agent; where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio between about 1:4 to about 4:1.

Also provided are compositions containing a nanoparticle containing a plurality of polymers, where at least a fraction of the polymers contain a hydrophobic polymer; a platinum-containing chemotherapeutic agent; and a topoisomerase inhibitor; where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio between about 1:4 to about 4:1.

By the term "polymer" is meant a molecular structure containing one or more repeat units (monomers) connected by covalent bonds. In some embodiments, the repeat units in a polymer can all be identical. In some embodiments, there can be more than one type of repeat unit present in a polymer (a copolymer). In some embodiments, the polymer is biologically derived, i.e., a biopolymer. In some embodiments, additional moieties can also be present in the polymer, e.g., targeting moieties, Pt-containing chemotherapeutic agents, and/or topoisomerase inhibitors, such as those described herein. In some embodiments, the polymer can be an amphiphilic polymer (e.g., an amphiphilic copolymer).

By the term "amphiphilic polymer" is meant a molecular structure containing one or more repeat units (monomers) connected by covalent bonds, that has both hydrophilic (polar) and lipophilic (apolar) properties. In some embodiments, an amphiphilic polymer can contain a hydrophobic polymer and a hydrophilic polymer.

By the term "targeting moiety" is meant a molecule that specifically binds to a molecule (e.g., a protein, lipid, or carbohydrate, or any combination thereof) present on the surface of a target mammalian cell (e.g., a target mammalian cell present in a mammal). Some of the compositions described herein contain a nanoparticle containing a targeting moiety linked to at least one of the plurality of polymers in the nanoparticle.

By the term "hydrophobic polymer" is meant a molecular structure containing one or more repeat units (monomers) connected by covalent bonds that is lipophilic (apolar). As is known in the art, a polymer can be characterized as being hydrophobic, e.g., based on the contact angle a droplet of water will make when placed on the polymer surface. If the contact angle is higher than 90°, then the polymer is considered hydrophobic. A polymer can also be characterized as being hydrophobic based on the surface tension of the polymer. If the surface tension of the polymer is higher than approximately 45 dynes/cm, then the polymer is considered hydrophobic.

On the other hand, a polymer can be characterized as being hydrophilic, e.g., based on the contact angle a droplet of water will make when placed on the polymer surface. If the contact angle is below 90°, then the polymer is considered hydrophilic. A polymer can also be characterized as being hydrophilic based on the surface tension of the polymer. If the surface tension of the polymer is lower than approximately 45 dynes/cm, then the polymer is considered hydrophilic.

By the term "topoisomerase inhibitor" is meant an agent that binds to a mammalian (e.g., human) topoisomerase enzyme and decreases a biological activity of the mammalian (e.g., human) topoisomerase enzyme. A topoisomerase inhibitor can be a topoisomerase I inhibitor and/or a topoisomerase II inhibitor. Non-limiting topoisomerase inhibitors are described herein. Additional topoisomerase inhibitors are known in the art.

The term "linked," as used herein, refers to a bond, e.g., a covalent or non-covalent linkage between two molecules. In some embodiments, a hydrophilic polymer (e.g., a first hydrophilic polymer) present within an amphiphilic polymer (e.g., an amphiphilic copolymer) can be linked to a targeting moiety, e.g., using any of the examples of methods described herein. In some embodiments, a hydrophobic polymer (e.g., a second hydrophobic polymer) can be linked to a platinum-containing chemotherapeutic agent, e.g., using any of the examples of methods described herein. In some embodiments, a hydrophobic polymer can be linked to a topoisomerase inhibitor, e.g., using any of the examples of methods described herein. In some embodiments, the two different molecules can be linked by an amide, an ester, or an ether bond.

The term "specific binding," as used herein, refers to binding between a first molecule and a binding partner that occurs to a substantially higher degree than binding of the first molecule to other, similar biological entities and other non-binding partners. In some embodiments, the first molecule binds to a binding party with a disassociation constant of less than about 1 µM (e.g., less than about 500 nM, less than about 100 nm, at least about 10 µM, or at least about 100 µM).

As used herein, a "synergistic" effect of a pair of molecules, compositions, or drugs, means that the combined effect is more than additive.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
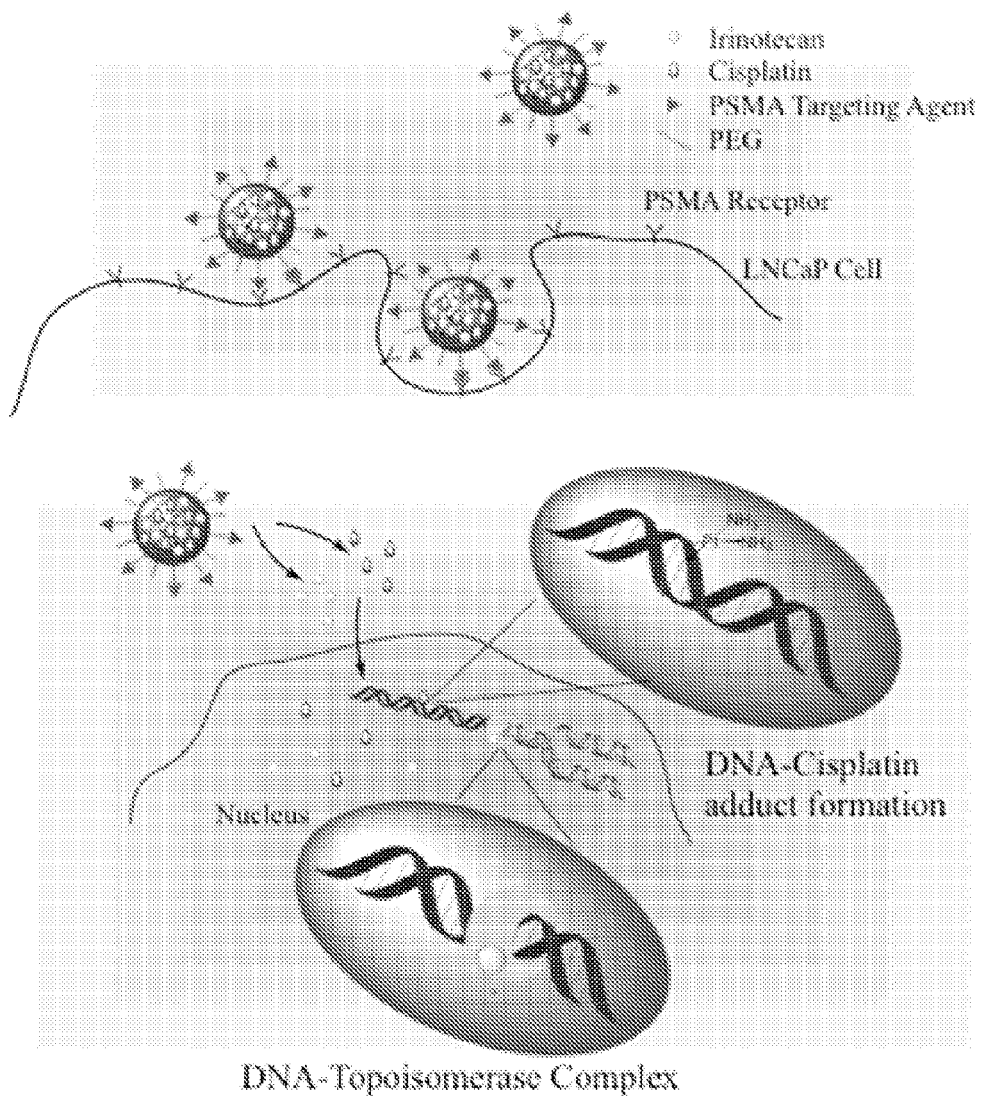
FIG. 1 is a schematic diagram showing the co-encapsulation of irinotecan (a topoisomerase inhibitor) and cisplatin (a platinum-containing chemotherapeutic agent) in a single nanoparticle targeted to prostate-specific membrane antigen (PMSA) receptors expressed on the surface of prostate cancer cells. Once the nanoparticles are taken up by the cells, the nanoparticles co-deliver irinotecan and cisplatin, and mediate a synergistic cytoxic effect in the prostate cancer cells.

The inventions described herein are based, at least in part, on the discovery that nanoparticles that contain both a Pt-containing chemotherapeutic drug and a topoisomerase inhibitor result in a significantly improved (synergistic) level of cancer cell inhibition, e.g., cancer cell death. In view of this discovery, provided herein are compositions that include a nanoparticle containing a plurality of polymers, where at least a fraction of the polymers contain a hydrophobic polymer linked to a platinum (Pt)-containing chemotherapeutic agent, and a topoisomerase inhibitor, where the polymers self-assemble in an aqueous liquid to form the nanoparticle, and where the fraction of the polymers containing a hydrophobic polymer form a hydrophobic core of the nanoparticle, and where the Pt-containing chemotherapeutic agent and the topoisomerase inhibitor are present within the hydrophobic core of the nanoparticle in a ratio between about 24:1 to about 1:24 (e.g., about 4:1 to about 1:4). In some embodiments, the nanoparticles further contain a targeting moiety linked to at least one of the polymers, where the targeting moiety is exposed on an outer surface of the nanoparticle. In some embodiments, the topoisomerase inhibitor is linked to at least one of the polymers. In some embodiments, the polymer containing a hydrophobic polymer is an amphiphilic polymer (e.g., an amphiphilic copolymer). In some embodiments, the polymer containing a hydrophobic polymer is hydrophobic polymer. In some embodiments, the nanoparticle contains a layer of a surfactant (e.g., an outer layer of a surfactant). A surfactant can be an anionic, cationic, or non-ionic surfactant.

The Pt-containing chemotherapeutic agent and the topoisomerase inhibitor are present within the hydrophobic core of the nanoparticle, e.g., in a ratio between about 24:1 to about 1:24 (e.g., between about 20:1 to about 1:20, between about 18:1 to about 1:18, between about 16:1 to about 1:16, between about 14:1 to about 1:14, between about 12:1 to about 1:12, between about 10:1 to about 1:10, between about 8:1 to about 1, between about 6:1 to about 1, between about 4:1 to about 1:4, and between about 4:1 to about 1:5:1). Also provided are methods of reducing the proliferation of a cancer cell and methods of treating cancer in a subject that include the use of the compositions described herein, as well as methods of making the nanoparticles described herein. Various, non-limiting features of each aspect of the invention are described below.

Compositions

The compositions described herein include one or more nanoparticles (e.g., targeted and/or non-targeted nanoparticles), and typically include 100s or many 1000s of nanoparticles, in an aqueous liquid, such as water, e.g., distilled or purified water, a buffer, or some other aqueous excipient. The nanoparticles described herein can have an average diameter of about 1000 nm or less, e.g., about 800 nm or less, 600 nm or less, 500 nm or less, 400 nm or less, 300 nm or less, 250 nm or less, 200 nm or less, 100 nm or less, 80 nm or less, 60 nm or less, 50 nm or less, or 40 nm or less. In some embodiments, the nanoparticles described herein have a mean diameter of between 20 nm to 100 nm, 30 nm to 90 nm, 40 nm to 80 nm, 50 nm to 70 nm, or 40 nm to 60 nm. In some embodiments, the compositions contain a plurality of the nanoparticles (e.g., targeted and/or non-targeted nanoparticles), and the nanoparticles have a polydispersity index of 0.8 or less, e.g., 0.6 or less, 0.4 or less, 0.2 or less, or 0.1 or less.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles. In some embodiments, no more than about 5% of the nanoparticles have a diameter greater than about 5%, about 3%, about 1%, about 0.3%, about 0.1%, about 0.03%, or about 0.01% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties.

For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition. In this regard, see, e.g., WO 2007/150030, which is incorporated herein by reference in its entirety.

Non-limiting examples of each constituent or component of the nanoparticles are described below. Any of the exemplary constituents described below can be used in any combination. In some embodiments, any of the exemplary constituents described below can be used with one or more corresponding constituents known in the art.

One skilled in the art will appreciate that similar nanoparticles can be made that include a plurality of polymers, wherein at least a fraction of the polymers contain a hydrophobic polymer linked to a first therapeutic agent, and a second therapeutic agent, wherein the polymers containing a hydrophobic polymer self-associate in an aqueous solution to form a nanoparticle with a hydrophobic core, and the first and second therapeutic agents are present in the hydrophobic core of the nanoparticle.

Examples of methods for generating the nanoparticles described herein are also provided below. Additional methods for generating the nanoparticles provided herein are known in the art.

Polymers Containing a Hydrophobic Polymer

A variety of different polymers that contain a hydrophobic polymer are known in the art. Non-limiting examples of hydrophobic polymers include, but are not limited to: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, aminoalkyl(meth)acrylamides), styrenes, and lactic acids.

A polymer that contains a hydrophobic polymer can be an amphiphilic polymer. Amphiphilic polymers contain a molecular structure containing one or more repeating units (monomers) connected by covalent bonds and the overall structure includes both hydrophilic (polar) and lipophilic (apolar) properties, e.g., at opposite ends of the molecule. In some embodiments, the amphiphilic polymers are copolymers containing a first hydrophilic polymer and a first hydrophobic polymer. Several methods are known in the art for identifying an amphiphilic polymer. For example, an amphiphilic polymer (e.g., an amphiphilic copolymer) can be identified by its ability to form micelles in an aqueous solvent and/or Langmuir Blodgett films.

In some embodiments, the amphiphilic polymer (e.g., amphiphilic copolymer) contains a hydrophilic polymer selected from the group of: polyethylene glycol (PEG), polyethylene oxide, polyethyleneimine, diethyleneglycol, triethyleneglycol, polyalkalene glycol, polyalkyline okxide, polyvinyl alcohol, sodium polyphosphate, polyvinylpyrrolidone, polyvinylmethylether, polymethyloxazoline, polyethyloxazoline, polyhydroxypropyl-oxazoline, polyhydroxypropylmethacrylamide, polymethacrylamide, polydimethylacryl-amide, polyhydroxypropylmethacrylate, polyhydroxyethylacrylate, hydroxymethylcellulose, hydroxyethylcellulose, polyglycerine, polyaspartamide, hyaluronic acid, polyoxyethlene-polyoxypropylene copolymer (poloxamer), lecithin, carboxylic acids (e.g., acrylic acid, methacrylic acid, itaconic acid, and maleic acid), polyoxyethylenes, polyethyleneoxide, and unsaturated ethylenic monocarboxylic acids.

In some embodiments, the amphiphilic polymer contains a hydrophobic polymer selected from the group of: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth) acrylamides), styrenes, and lactic acids.

In some embodiments, the amphiphilic polymer contains PLA-PEG, PLGA-PEG (e.g., the amphiphilic polymer is PLGA-PEG), polystyreneblock-polyethyleneoxide, polybutylacrylate-b-polyacrylicacid, or polybutylmethacrylate-b-polyethyleneoxide. Additional examples of amphiphilic copolymers are described in U.S. Patent Application Publication No. 2004/0091546 (incorporated herein by reference in its entirety). Additional examples of amphiphilic polymers (e.g., amphiphilic copolymers) are known in the art.

In some implementations, the amphiphilic polymer contains as the hydrophilic portion a poly(ethylene glycol) ("PEG"), having the formula —(CH$_2$—CH$_2$—O)n-, where n is any positive integer of n from 20 to 500 (corresponding approximately to PEG with a molecular weight between about 1,000 to 20,000). In some embodiments, the amphiphilic polymer (e.g., amphiphilic copolymer) contains a branched PEG (see, e.g., Veronese et al., *BioDrugs* 22:315-329, 2008; Hamidi et al., *Drug Deliv.* 13:399-409, 2006). Methods for generating an amphiphilic polymer (e.g., amphiphilic copolymer) that contains a PEG are known in the art (e.g., by using 1-ethyl-3-(3-dimethylarninopropyl) carbodiimide hydrochloride) and NHS (N-hydroxysuccinimide) to react a polymer to a PEG group terminating in an amine, e.g., by ring opening polymerization techniques (ROMP)). In some embodiments, the amphiphilic polymers are joined by ester bonds (e.g., R—C(O)—O—R' bonds) and/or ether bonds (e.g., R—O—R' bonds). An exemplary method for generating an amphiphilic polymer is described in Example 1. Thus, in some embodiments, the amphiphilic polymers can comprise PLGA-PEG.

Targeting Moieties

In some embodiments, targeting moieties can be used to direct the nanoparticles, once administered to a subject, to move within the subject, e.g., through the bloodstream, the lymphatic system, or a tissue or organ, and accumulate at and bind to a particular mammalian (e.g., human) cell type, collection of mammalian (e.g., human) cells, tissue, or organ. The "directing" is passive, in the targeting moieties typically do not provide any motive force, but enable the nanoparticles to bind to a specific cell or a specific receptor or molecule on the surface of a cell. Thus, as the targeted nanoparticles move throughout the circulatory system, they bind, and thus accumulate, in a predetermined location. In some embodiments, the targeting moieties direct the nanoparticles to a particular mammalian (e.g., human) cancer cell present in a mammal. The targeting moieties, when present in nanoparticles, should be present on an outer surface of the nanoparticles, at least at some point in time, so that they can interact with, e.g., specifically bind to, cellular targets, e.g., binding ligands, receptors, or cell surface markers and signalizing molecules. Thus, in some implementations, the targeting moieties present in the targeted nanoparticles are linked to a hydrophilic portion or polymer present in one of the polymers present in the nanoparticle. In some embodiments, the targeting moiety may be located within the hydrophobic core of a nanoparticle when the nanoparticle is administered to the blood stream, and over time the targeting moieties become exposed at the surface of the hydrophilic shell so that they can provide their targeting effect.

A variety of suitable targeting moieties are known in the art (see, e.g., Cotten et al., Methods Enzvm. 217:618, 1993; Torchilin, Eur. J. Pharm. Sci. 11:881, 2000; Garnett, Adv. Drug Deliv. Rev. 53:171, 2001). For example, any of a number of different targeting moieties that bind to antigens on the surfaces of target cells (e.g., mammalian cancer cells) can be employed. In some embodiments, the targeting moiety is an antibody or an antigen-binding antibody fragment that can specifically bind to target cell surface antigens (e.g., a tumor antigen). In some embodiments, the targeting moiety is an antigen-binding antibody fragment, e.g., a Fab, a Fab', or a F(ab')$_2$ fragment. Exemplary antigen-binding antibody fragments suitable for use in forming the amphiphilic copolymers linked to a targeting moiety are already available in the art. In some embodiments, the targeting moiety is a ligand for a receptor on the surface of a target cells. In some embodiments, the targeting moiety can be a small molecule or biomolecule (natural or synthetic) that binds specifically to a cell surface receptor, protein, glycoprotein, or lipid, or a combination thereof, found on the surface of the desired target cell. In some embodiments, the small molecule is S,S-2[3-][5-amino-1-carboxypentyl]-ureido]-pentanedioic acid (LIG), which specifically binds to the prostate-specific membrane antigen (PSMA).

Non-limiting examples of targeting moieties include a peptide, a protein, an enzyme, a nucleic acid, a fatty acid, a hormone, an antibody, an antigen-binding antibody fragment, a carbohydrate, a peptidoglycan, a glycopeptide, or the like. These and other targeting moieties are discussed in detail below. The targeting moieties can have a molecular weight of at least about 1,000 Da, at least about 2,500 Da, at least about 3000 Da, at least about 4000 Da, or at least about 5,000 Da. Relatively large targeting moieties can be useful, in some cases, for differentiating between cells (e.g., differentiating between cancer and non-cancer mammalian cells). In some embodiments, a targeting moiety can offer smaller dissociation constants. e.g., tighter binding, to the target cell. In some embodiments, the targeting agent can be relatively small, for example, having a molecular weight of less than about 1,000 Da or less than about 500 Da.

In some embodiments, the targeting moieties include a protein or a peptide. Generally, peptides are amino acid sequences of less than about 100 amino acids in length, but can include sequences of up to 300 amino acids. Proteins generally are considered to be molecules of at least 100 amino acids. In some embodiments, the protein targeting moiety can be a protein drug, an antibody, an antigen-binding antibody fragment, a recombinant antibody, a recombinant protein, an enzyme, or the like. In some embodiments, one or more of the amino acids of the protein or peptide can be modified, for example, by the addition of a chemical entity such as a carbohydrate group, a phosphate group, a farnesyl group, an isofarnesyl group, a fatty acid group, a linker for conjugation, functionalization, and/or other modification.

Additional examples of peptide or protein targeting moieties include, but are not limited to, ankyrins, arrestins, bacterial membrane proteins, clathrin, connexins, dystrophin, endothelin receptor, spectrin, selectin, cytokines, chemokines, growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors (e.g., genistein), steroids, glycoproteins (e.g., ABC transporters), platelet glycoproteins, GPIb-IX complex, GPIIb-IIIa complex, vitronectin, thrombomodulin, CD4, CD55, CD58, CD59, CD44, CD168, lymphocyte function-associated antigen, intercellular adhesion molecule, vascular cell adhesion molecule, Thy-1, antiporters, CA-15-3 antigen, fibronectins, laminin, myelin-associated glycoprotein. GAP, and GAP43. In some embodiments, the targeting moiety includes an affibody, a nanobody, an Avimer, an Adnectin, a domain antibody, and a small modular immunopharmaceutical (Trubion Pharmaceuticals Inc., Seattle, Wash.).

In some embodiments, the targeting moiety is a CLT1 or CLT2 peptide, which binds to fibrin-fibronectin complexes in blood clots. Additional peptide targeting moieties that can specifically bind to cells in the brain, kidneys, lungs, skin, pancreas, intestine, uterus, adrenal gland, and prostate are known in the art (e.g., see Pasqualini et al., Mol. Psychiatry 1:421-2 (1996), and Rajotte et al., J. Clin. Invest. 102:430-437, 1998).

In some embodiments, the targeting moiety includes a cytokine or cytokine receptor, such as Interleukin-1 (IL-1), IL-2, IL-3, IL-4, IL-5, IL-6, IL-7, IL-8, IL-9, IL-10, IL11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor. IL-8 receptor. IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon alpha, interferon beta, or interferon gamma. In some embodiments, the targeting moiety contains a transferrin receptor or a folate receptor.

In some embodiments, the targeting moiety includes a growth factor and protein hormone, e.g., erythropoietin, angiogenin, hepatocyte growth factor, fibroblast growth factor, keratinocyte growth factor, nerve growth factor, tumor growth factor alpha, thrombopoietin, thyroid stimulating factor, thyroid releasing hormone, neurotrophin, epidermal growth factor, VEGF, ciliary neurotrophic factor, LDL, somatomedin, insulin growth factor, or insulin-like growth factor I and II.

In some embodiments, the targeting moiety includes a chemokine, e.g., ENA-78, ELC, GRO-alpha, GRO-beta, GRO-gamma, HRG, LIF, IP-10, MCP-1, MCP-2, MCP-3, MCP-4, MIP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors (e.g., CXCR1, CXCR2, CXCR3, CXCR4, CXCR5, CXCR6, or CXCR7), or beta-chemokine receptors (e.g., CCR1, CCR2, CCR3, CCR4, CCR5, CCR6, or CCR7).

In some embodiments the targeting moiety binds to components of the extracellular matrix ("ECM"), e.g., glycosaminoglycan ("GAG") and collagen. In some embodiments, the targeting moiety contains a pathogen-associated molecular pattern (PAMP) that targets a Toll-like Receptor (TLR) on the surface of target cell or tissue. Non-limiting examples of PAMPs that can serve as a targeting moiety include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins, such as MALP-2 (bacterial), flagellin (bacterial), poly(inosinic-cytidylic)acid (bacterial), lipoteichoic acid (bacterial), or imidazoquinolines (synthetic).

In some embodiments, the targeting moiety can be a lectin that targets mucin or mucosal cell layers. Non-limiting examples of lectins that can be used as a targeting moiety include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glyrine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A and Succinyl-Concanavalin A, and the lectins from *Triticum vulgaris, Ulex europaeus* I, II, and III. *Sambucus nigra, Maackia amurensis, Limax fluvus, Homarus americanus, Cancer antennarius,* and *Lotus tetragonolobus.*

In some embodiments, the targeting moiety specifically binds to a target antigen, e.g., prostate-specific membrane antigen (PSMA), HER-2, HER-3, EGFR, and folate receptor. PSMA is a well-established tumor marker, which is up-regulated in prostate cancer, particularly in advanced, hormone-independent, and metastatic disease (Ghosh and Heston, *J. Cell. Biochem.* 91:528-539, 2004). PSMA has been employed as a tumor marker for imaging of metastatic prostate cancer and as a target for experimental immunotherapeutic agents. PSMA is the molecular target of ProstaScint®, a monoclonal antibody-based imaging agent approved for diagnostic imaging of prostate cancer metastases. J591, a de-immunized monoclonal antibody that targets the external domain of PSMA, has been evaluated clinically as an agent for radioimmunotherapy and radioimmunoimaging. Radiolabeled J591 is reported to accurately target prostate cancer metastases in bone and soft tissue, and to display anti-tumor activity. Interestingly, PSMA is differentially expressed at high levels on the neovasculature of most non-prostate solid tumors, including breast and lung cancers, and the clinical feasibility of PSMA targeting for non-prostate cancers was recently demonstrated in two distinct clinical trials (Morris et al., *Clin. Cancer Res.* 13:2707-2713, 2007; Milowsky et al., *J. Clin. Oncol.* 25:540-547, 2007). The highly restricted presence of PSMA on prostate cancer cells and non-prostate solid tumor neovasculature makes it an attractive target for delivery of cytotoxic agents to most solid tumors.

In some embodiments, the targeting moiety can be an antibody or an antigen-binding antibody fragment. An antibody typically refers to a protein or glycoprotein consisting of one or more polypeptides substantially encoded by an immunoglobulin gene or a fragment of an immunoglobulin gene (e.g., a variable domain of a light or heavy chain immunoglobulin gene). The immunoglobulin gene can include a kappa, lambda, alpha, gamma, delta, epsilon, and mu constant region gene, and/or an immunoglobulin variable region gene. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases or produced by molecular biology techniques known in the art.

Non-limiting examples of targets of any of targeting moieties described herein (e.g., antibodies or antigen-binding antibody fragments) include: anti-cluster of differentiation antigens CD-1 through CD-166, cytokines (e.g., IL-1 through anti-IL-18), immune receptors (e.g., T cell receptors, major histocompatibility complexes I and II, and B cell receptors), selectin killer inhibitory receptors, killer activating receptors, OX-40, MadCAM-1, Gly-CAM 1, integrins, cadherens, sialoadherens, Fas, CTLA-4, Fc-gamma receptor, Fc-alpha receptors, Fc-epsilon receptors, Fc-mu receptors, anti-metalloproteinase antibodies (e.g., collagenase, MMP-1 through MMP-8, TIMP-1, and TIMP-2), anti-cell lysis/proinflammatory molecules (e.g., perforin, complement components, prostanoids, nitrous oxide, and thromboxanes), and adhesion molecules (e.g., carcinoembryonic antigens, lamins, or fibronectins).

In some embodiments, the targeting moiety is a nucleic acid (e.g., an aptamer) that specifically binds to a certain target molecule on the surface of the desired target cell (e.g., a prostate cancer cell). A nucleic acid targeting moiety is a nucleic acid that can be used to bind to a specific molecule present on a target cell. Nucleic acid or oligonucleotide refer generally to a polymer of nucleotides. A nucleotide is a molecule containing a sugar moiety, a phosphate group, and a base (usually nitrogenous). Typically, a nucleotide contains one or more bases connected to a sugar-phosphate backbone (a base connected only to a sugar moiety, without the phosphate group, is a "nucleoside"). The sugars within a nucleotide can be, for example, ribose sugars (a "ribonucleic acid," or "RNA"), or deoxyribose sugars (a "deoxyribonucleic acid," or "DNA"). In some cases, a nucleic acid can contain both ribose and deoxyribose sugars. Examples of bases include, but not limited to, the naturally-occurring bases (e.g., adenosine or "A," thymidine or "T," guanosine or "CG" cytidine or "C," or uridine or "U"). In some cases, the nucleic acid can also contain a nucleoside analog (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), a chemically- or biologically-modified base (e.g., a methylated base), an intercalated base, a modified sugar (e.g., 2'-fluororibose, 2'-aminoribose, 2'-azidoribose, 2'-O-methylribose, L-enantiomeric nucleosides arabinose, or hexose), a modified phosphate moiety (e.g., a phosphorothioate or 5'-N-phosphoramidite linkage), and/or any other naturally and non-naturally occurring bases substitutable into the nucleic acid, including substituted and unsubstituted aromatic moieties. Other suitable base and/or polymer modifications are well-known to those skilled in the art. In some embodiments, the nucleic acid can include DNA, RNA, modified DNA, modified RNA, antisense oligonucleotides, expression plasmid systems, nucleotides, modified nucleotides, nucleosides, modified nucleosides, intact genes, or combinations thereof. Additional examples of nucleic acids include interfering RNA, natural or unnatural siRNAs, shRNAs, microRNAs, ribozymes, DNA plasmids, antisense oligonucleotides, randomized oligonucleotides, or ribozymes.

In some embodiments, the targeting moiety is pegaptanib, a pegylated anti-VEGF aptamer. Although the pegaptanib aptamer was originally approved by FDA in 2004 to treat age-related macular degeneration (AMD) disease, it has the potential to target prostate cancer cells because it binds specifically to VEGF 165: a protein recognized as the key inducer of tumor angiogenesis. In some embodiments, the targeting moiety is Aptamer O-7 which binds to osteoblasts, A10 RNA aptamer which binds to prostate cancer cells, TTA1 aptamer which binds to breast cancer cells, or A9 RNA aptamer (Javier et al., *Bioconjug. Chem.* 19(6):1309-1312, 2008). Additional target molecules are also described in U.S. Patent Application Publication No. 2009/0105172. In general, aptamers are stable in a wide range of pH (~4-9), physiological conditions, and solvents. Aptamers are known to be less immunogenic than antibodies and can penetrate a tumor more easily because of their size. The shape of aptamer binding sites, which includes grooves and clefts, provide highly specific characteristics and drug-like capabilities.

In some embodiments, a nanoparticle can at least two different types of polymers (e.g., two different amphiphilic polymers) linked to one or two, or more, different types of targeting moiety, e.g., where a first polymer is linked a first targeting moiety and a second polymer is linked to a second targeting moiety. In some embodiments, the first and second targeting moieties specifically bind to the same target cell (or two different target cells). In some embodiments, the first targeting moiety binds specifically to an immune system cell (e.g., a leukocyte or T-cell) and the second targeting moiety targets a cancer cell. Other targeting agents include agents that specifically bind to biological targets such as a particular immune system cell (e.g., a T cell or B cell), a protein, an enzyme, or other circulating agent in a subject. In some embodiments, the targeting moiety is a heat shock protein HSP70 for binding to dendritic cells, or folic acid for binding to cancer cells. In some embodiments, the targeting moiety is a polysaccharide or sugar (e.g., silylic acid for targeting leucocytes), a toxin (e.g., saporin), or an antibody (e.g., an antibody that specifically binds to CD2, CD3, or CD28 on T-cells).

Additional examples of targeting moieties are described in WO 2008/124632, which is incorporated herein by reference in its entirety. Other targeting moieties are known in the art are contemplated for use with the present disclosure.

Linking a Targeting Moiety to a Polymer

Any of polymers (e.g., amphiphilic polymers, hydrophilic polymers, and hydrophilic polymers) described herein (or any of the amphiphilic polymers or hydrophilic polymers known in the art) can be linked to a targeting moiety using methods known in the art (e.g., linked through a hydrophilic polymer present in an amphiphilic polymer (e.g., an amphiphilic copolymer)). Non-limiting examples of linking a targeting moiety to a hydrophilic polymer present in an amphiphilic polymer are described below. For example, in some embodiments, a hydrophilic polymer present in an amphiphilic polymer can be linked to a targeting moiety through an ester, an amide, or an ether bond. The targeting moiety should be attached to the hydrophilic polymer present in the amphiphilic polymer in a manner that results in the presence of the targeting moiety on an outer surface of the shell of the nanoparticle. For example, the targeting moiety can be attached to the amphiphilic polymer in a portion of the amphiphilic polymer that has hydrophilic or polar properties.

To generate an amphiphilic polymer or hydrophilic polymer linked to a targeting moiety, the amphiphilic polymer or hydrophilic polymer can be prepared with a pendant functional group, i.e., a functional group present within the hydrophilic polymer present in the amphiphilic polymer or hydrophilic polymer for conjugation to a targeting moiety. In some embodiments, the amphiphilic polymer or hydrophilic polymer can be prepared with approximately one functional group (e.g., linked functional group) for every 1, 2, 3, 4, 5, 6, 7, 8, 9, 10, 12, 15, or 20 monomer units (e.g., hydrophilic polymer units) of the amphiphilic polymer or hydrophilic polymer. In some embodiments, the functional groups can be restricted to one portion of the amphiphilic polymer (e.g., a first hydrophilic polymer present in an amphiphilic polymer). In some embodiments, the functional group can be a hydroxyl, carboxyl, amine, amide, carbamate, maleimide, thiol, halide, azide, proparzyl, or allyl. In some embodiments, the functional group can be joined to the amphiphilic polymer or hydrophilic polymer by a linker.

Various methods are known to link a heterofunctional linker to a targeting moiety using covalent bonds (e.g., through σ-bonding, π-bonding, metal to non-metal bonding, agnostic interactions, disulfide bonds, and three-center two-electron bonds). In some embodiments, a bond, e.g., cross-linking, can be achieved by forming an amide bond between carboxyl (or maleimide) and a primary amine by using 1-ethyl-3-[3-dimethylaminopropyl]carbodiimide hydrochloride/N-hydroxysuccinimide (EDC/NHS) or benzotriazole-1-yl-oxy-tris-pyrrolidino-phosphonium hexafluorophosphate/N-hydroxybenzotriazole (pyBOP/HOBt). The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

In another example, the linkage, e.g., crosslinking, is formed between maleimide and sulfhydryl (thiol) groups in both aqueous and organic solvents. A reduction cleavable crosslinking can be achieved between sulfhydryl (thiol) group, through the pyridylthiol group, 3-nitro-2-pyridylthio (Npys) group, and Boc-S-tert-butylmercapto (StBu) group. The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

Methods of making functionalized amphiphilic polymers with pendant functional groups are known in the art. For example, methods of making functionalized polylactides, polyglycolides, and polyesteramides are described in Gerhardt et al. (*Biomacromolecules* 7:1735-1742, 2006). Synthesis of functionalized dilactones and their use in the preparation of polyesters with hydroxyl functional groups, poly(lactic acid-co-hydroxymethyl glycolic acid) and poly (lactic acid-co-glycolic acid-co-hydroxymethyl glycolic acid) is described in Leemhuis et al. (*Biomacromolecules* 8:2943-2949, 2007), Leemhuis et al. (*Eur. J. Org. Chem.*, 3344-3449, 2003) and Leembuis et al. (*Macromolecules* 39:3500-3508, 2007). Hydroxymethyl- and succinylated-PLA polymers are described in Noga et al. (*Biomacromolecules* 9:2056-2062, 2008). Poly hexyl-substituted lactides are disclosed in Trimaille et al. (*Chimia* 59:348-352, 2005) and Trimaille et al. (*J. Biomed. Mater. Res.* 80A:55-65, 2007). Jing et al. (*J. Am. Chem. Soc.* 130:13826-27, 2008) describes PLA with functional bicyclic esters. Poly($\alpha$-hydroxy acid)s with pendant carboxyl groups are disclosed in Kimura et al. (*Macromolecules* 21:3338-40, 1988). In some embodiments, the polymers can be functionalized by "click" methods, as described in Jiang et al. (*Macromolecules* 41:1937-44, 2008).

Additional non-limiting methods of synthesis and linkage of amphiphilic polymers with targeting moieties are disclosed in U.S. Patent Application Publication No. 20080248126 and WO 2011/084620, each of which are incorporated herein by reference in their entireties.

The length of the amphiphilic polymers or hydrophilic polymers, e.g., having pendant functional groups, which are linked to a targeting moiety, can be varied to provide desired parameters. In some embodiments, the amphiphilic polymer or hydrophilic polymer has a molecular weight of about 2000 g/mol, e.g., about 3000 g/mol, about 4000 g/mol, about 5,000 g/mol, about 10,000 g/mol, about 20,000 g/mol, about 50,000 g/mol, or about 100,000 g/mol, before linkage to the targeting moiety.

In some embodiments, a targeting moiety can be linked to an amphiphilic polymer or hydrophilic polymer using di-tert-butyl dicarbonate chemistry, carboiimide (e.g., 1-ethyl-3-(3-dimethylaminopropyl) carbodiimide) and N-hydroxucinimide (NHS) chemistry, reaction of sufhydryl with sufhydryl reactive groups (e.g., maleimide, haloacetyls, and pyridyl disulfides), reaction of carbonyl with carbonyl reactive groups (e.g., hydrazides and alkoxyamines), and click chemistry (e.g., azide-alkyne-cycloaddition). A non-limiting example of generating a PLGA-PEG linked to a small molecule targeting moiety (LIG) is described in Example 1.

Hydrophobic Polymers Linked to a Pt-Containing Chemotherapeutic Agent

One constituent of the nanoparticles described herein is a polymer containing a hydrophobic polymer linked to a Pt-containing chemotherapeutic agent. The components of a polymer containing a hydrophobic polymer linked to a Pt-containing chemotherapeutic agent, as well as methods of making them, are described below.

A hydrophobic polymer is one that generally repels water. A hydrophobic polymer can be identified, for example, by preparing a sample of the polymer and measuring its contact angle with water (typically, a hydrophobic polymer will have a contact angle of greater than about 500).

In some embodiments, the plurality of polymers contained in the nanoparticle include at least two (e.g., at least three, four, or five) different polymers containing a hydrophobic polymer. For example, a nanoparticle can contain an amphiphilic polymer and a second hydrophobic polymer, where the amphilic polymer and/or the hydrophobic polymer is linked to a Pt-containing chemotherapeutic agent.

Non-limiting examples of hydrophobic polymers include: polylactic acid (PLA), polypropylene oxide, poly(lactide-co-glycolide) (PLGA), poly(epsilon-caprolactone), poly (ethylethylene), polybutadiene, polyglycolide, polymethylacrylate, polyvinylbutylether, polystyrene, polycyclopentadienyl methylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth) acrylamides), styrenes, and lactic acids.

In some embodiments, the hydrophobic polymer is PLA. In some embodiments, the Pt-containing chemotherapeutic agent linked to at least a fraction of the polymers containing a hydrophobic polymer is cisplatin. In some embodiments, the polymer containing a hydrophobic polymer that is linked to a Pt-containing chemotherapeutic agent is PLA-cisplatin.

Pt-Containing Chemotherapeutic Agents

A variety of different Pt-containing chemotherapeutic agents that can be linked to a polymer containing a hydrophobic polymer (e.g., an amphiphilic polymer) are known in the art. Non-limiting examples of Pt-containing chemotherapeutic agents include cisplatin, carboplatin, oxaliplatin, satraplatin, picoplatin, aroplatin, and phenatriplatin. In the nanoparticles described herein, the Pt-containing chemotherapeutic agent is located within the hydrophobic core of the nanoparticles.

In some embodiments, the Pt-containing chemotherapeutic agent is a platinum prodrug. Pt-containing chemotherapeutic agents include platinum pro-drugs that can contain platinum (IV) with two axial ligands attached, which upon reduction becomes platinum(II). Non-limiting examples of platinum prodrugs include cis,trans,cis-[Pt(NH$_3$)$_2$(XY)C$_{12}$], cis,trans,cis-[Pt(NH$_3$)$_2$(XY)(CBDCA)], and cis,trans,cis-[Pt (DACH)XY)(Ox)], where X and Y are the axial ligands that would leave upon subsequent bioreduction of the resulting platinum(IV) compound to yield the platinum(II) active drug. CBDCA is cyclobutane-1,1,-dicarboxylate, DACH is R,R-1,2-diaminocyclohexane, and Ox is oxalate. The platinum prodrug can be linked to at least a fraction of the polymers containing a hydrophobic polymer. X and Y can be different. X or Y can be attached directly to polymer containing a hydrophobic polymer or attached to the polymer containing a hydrophobic polymer through a linker. X and/or Y could be attached to the polymer containing a hydrophobic polymer, but not necessarily both.

Linkage of a Pt-Containing Chemotherapeutic Agent to a Hydrophobic Polymer

Any of the examples of polymers containing a hydrophobic polymers described herein or any of the polymers containing a hydrophobic polymer known in the art can be linked to a Pt-containing chemotherapeutic agent (e.g., any of the Pt-containing chemotherapeutic agents described herein) using methods known in the art. Non-limiting examples of linking a Pt-containing chemotherapeutic agent to a polymer containing a hydrophobic polymer are described below. Additional non-limiting examples of linking a Pt-containing chemotherapeutic agent to a polymer containing a hydrophobic polymer are known in the art. In some embodiments, a polymer containing a hydrophobic polymer can be linked to a Pt-containing chemotherapeutic agent through an ester, an amide, or an ether bond.

To generate a polymer containing a hydrophobic polymer linked to a Pt-containing chemotherapeutic agent, the polymer containing a hydrophobic polymer can be prepared with a pendant functional group, i.e., a functional group present along a length of the polymer, e.g., a portion of the polymer, for linkage to a targeting moiety. In some embodiments, the polymer containing a hydrophobic polymer can be prepared with approximately one functional group (e.g., linked functional group) for every 1, 2, 3, 4, 5, 6, 7, 8, 9, 10, 12, 15, or 20 monomer units of the polymer containing a hydrophobic polymer. The functional groups can be restricted to one portion of the polymer containing a hydrophobic polymer. In some embodiments, the functional group can be a hydroxyl, carboxyl, amine, amide, carbamate, maleimide, thiol, halide, azide, proparzyl, or allyl. In some embodiments, the functional group can be joined to the polymer containing a hydrophobic polymer by a linker.

Various methods are known to link a heterofunctional linker to a targeting moiety using covalent bonds (e.g., through α-bonding, π-bonding, metal to non-metal bonding, agnostic interactions, disulfide bonds, and three-center two-electron bonds). In some embodiments, a linkage, e.g., crosslinking, can be achieved by forming an amide bond between carboxyl (or maleimide) and a primary amine by using 1-ethyl-3-[3-dimethylaminopropyl]carbodiimide hydrochloride/N-hydroxysuccinimide (EDC/NHS), benzotriazole-1-yl-oxy-tris-pyrrolidino-phosphonium hexafluorophosphate/N-hydroxybenzotriazole (pyBOP/HOBt), or N,N-dicyclohexyl carbodiimide (DCC)/HOBt. The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

In another example, the linkage, e.g., crosslinking, is formed between maleimide and sulfhydryl (thiol) groups in both aqueous and organic solvents. A reduction cleavable crosslinking can be achieved between sulfhydryl (thiol) group, through the pyridylthiol group, 3-nitro-2-pyridylthio (Npys) group, and Boc-S-tert-butylmercapto (StBu) group. The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

Methods of making functionalized polymers containing a hydrophobic polymer with pendant functional groups are known in the art. For example, methods of making and functionalized polylactides, polyglycolides, and polyesteramides are described in Gerhardt et al. (*Biomacromolecules* 7:1735-1742, 2006). Synthesis of functionalized dilactones and their use in the preparation of polyesters with hydroxyl functional groups, poly(lactic acid-co-hydroxymethyl glycolic acid) and poly(lactic acid-co-glycolic acid-co-hydroxymethyl glycolic acid) is described in Leemhuis et al. (*Biomacromolecules* 8:2943-2949, 2007), Leemhuis et al. (*Eur. J. Org. Chem.* 3344-3449, 2003), and Leemhuis et al. (*Macromolecules* 39:3500-3508, 2007). Hydroxymethyl- and succinylated-PLA polymers are described in Noga et al. (*Biomacromolecules* 9:2056-2062, 2008). Poly hexyl-substituted lactides are disclosed in Trimaille et al. (*Chimia* 59:348-352, 2005); and Trimaille et al. (*J. Biomed. Mater. Res.* 80A:55-65, 2007). Jing et al. (*J. Am. Chem. Soc.* 130:13826-27, 2008) describes PLA with functional bicyclic esters. Poly(α-hydroxy acid)s with pendant carboxyl groups are disclosed in Kimura et al. (*Macromolecules* 21:3338-40, 1988). In some embodiments, the polymers can be functionalized by "click" methods, as described in Jiang et al. (*Macromolecules* 41:1937-44, 2008).

Additional non-limiting methods that can be used to link a polymer containing a hydrophobic polymer with Pt-containing chemotherapeutic agents are disclosed in U.S. Patent Application Publication No. 20080248126 and WO 2011/084620, each of which are incorporated herein by reference.

The length of the polymer containing a hydrophobic polymer, e.g., having pendant functional groups, which are linked to a Pt-containing chemotherapeutic agent, can be varied to provide desired parameters. In some embodiments, the polymer containing a hydrophobic polymer has a molecular weight of about 2000 g/mol, e.g., about 3000 g/mol, about 4000 g/mol, about 5,000 g/mol, about 10,000 g/mol, about 20,000 g/mol, about 50,000 g/mol, or about 100,000 g/mol, before linkage to the Pt-containing chemotherapeutic moiety. In some embodiments, a Pt-containing chemotherapeutic agent can be linked to a polymer containing a hydrophobic polymer using di-tert-butyl dicarbonate chemistry. A non-limiting example of generating a PLA linked to cisplatin is described in Example 1.

Topoisomerase Inhibitors

Topoisomerase inhibitors are agents that have the ability to bind and decrease (e.g., a detectable decrease) an activity of a mammalian (e.g., human) topoisomerase enzyme (e.g., human topoisomerase I (e.g., NCBI Accession No. AAA61207.1) or human topoisomerase II (e.g., NCBI Accession No. CAA48197.1). In some embodiments, the topoisomerase inhibitor is a topoisomerase I inhibitor. In some embodiments, the topoisomerase inhibitor is a topoisomerase II inhibitor. In some embodiments, the topoisomerase inhibitor is linked to at least one of the plurality of polymers containing a hydrophobic polymer. For example, the topoisomerase inhibitor (e.g., irinotecan) can be linked to PLA. In some embodiments, the nanoparticles contain PLGA-PEG, PLA-cisplatin, and PLA-irinotecan.

A variety of topoisomerase activity assays are known in the art (see, e.g., Yalowich et al., *Biochem. Pharmacol.* e-published April 2012, and Liu et al., *Toxicol. Lett* 211: 126-134, 2012). Non-limiting examples of topoisomerase inhibitors that can be included in the nanoparticles described herein are irinotecan. SN-38, topotecan, camptothecin, and lamellarin D. In some embodiments, two or more topoisomerase inhibitors are included in the nanoparticles. In some embodiments, at least one topoisomerase I and at least one topoisomerase IT inhibitor are included in the nanoparticles. In some embodiments, the toposimerase inhibitor is irinotecan. Additional examples of topoisomerase inhibitors are known in the art.

Biocompatibility and Biodegradability of the Nanoparticles

The nanoparticles described herein are biodegradable and/or biocompatible, i.e., a nanoparticle containing polymers that do not typically induce an adverse response when inserted or injected into a living subject, for example, without significant inflammation and/or acute rejection of the polymers by the immune system, for instance, via a T-cell response. One simple test to determine biocompatibility is to expose polymers to cells in vitro, where biocompatible polymers typically do not result in significant cell death at moderate concentrations, e.g., at concentrations of about 50 µg/$10^6$ cells. For example, a biocompatible polymer may cause less than about 20% cell death when exposed to cells such as fibroblasts or epithelial cells, even if phagocytosed or otherwise taken-up by such cells.

Non-limiting examples of biocompatible polymers include polydioxanone (PDO), polyhydroxyalkanoate, polyhydroxybutyrate, poly(glycerol sebacate), polyglycolide, polylactide, polycaprolactone, or polyanhydride, or copolymers or derivatives including these and/or other polymers.

The polymers present in the nanoparticles can also be biodegradable, i.e., the polymers are able to degrade, chemically and/or biologically, within a physiological environment, such as within the body. For instance, the polymers can hydrolyze spontaneously upon exposure to water (e.g., within a subject) and/or the polymers can degrade upon exposure to heat (e.g., at temperatures of about 37° C.). Degradation of the polymers can occur at varying rates, depending on the polymers or copolymers used. For example, the half-life of the polymers (the time at which 50% of the polymers are degraded into monomers and/or other nonpolymeric moieties) can be on the order of days, weeks, months, or years, depending on the particular polymers used to make the nanoparticles. The polymers can be biologically degraded, e.g., by enzymatic activity or cellular machinery, in some cases, for example, through exposure to a lysozyme (e.g., having relatively low pH). In some cases, the polymers can be broken down into monomers and/or other nonpolymeric moieties that cells can either reuse or dispose of without significant toxic effect on the cells (e.g., polylactide can be hydrolyzed to form lactic acid, and polyglycolide can be hydrolyzed to form glycolic acid).

Non-limiting examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, e.g., poly(lactide-co-glycolide) (PLGA).

Additional Anti-Cancer Agents

In some embodiments, the nanoparticles can contain one or more additional anti-cancer agents, either in the hydrophobic core or attached on a surface of the hydrophilic shell. In some embodiments, the additional anti-cancer agent is an alkylating agent (e.g., cyclophosphamide, mechlorethamine, uramustine, melphalan, chorambucil, ifosfamide, carmustine, lomustine, streptozocin, busulfan, and thiotepa). In some embodiments, the additional anti-cancer agent is an antimetabolite (e.g., a purine analogue, a pyrimidine analogue, or an antifolate). In some embodiments, the additional anti-cancer agent is an antracycline (e.g., daunorubicin, epirubicin, idarubicin, valrubicin, and mitoxantrone). In some embodiments, the additional anti-cancer agent is a plant alkyloid or a therapeutic antibody (or antigen-binding antibody fragment) that specifically binds to a tumor antigen. In some embodiments, the additional anti-cancer agent is linked to a polymer present in the nanoparticle (e.g., present in the hydrophobic core of the nanoparticle).

Controlled Release

In some embodiments, the compositions are formulated for controlled-release. In some embodiments, controlled release can be achieved by implants. Nanoparticle drug-delivery compositions can release the linked active agents (e.g., a Pt-containing chemotherapeutic agent and topoisomerase inhibitor) through surface or bulk erosion, diffusion, and/or swelling followed by diffusion, in a time- or condition-dependent manner. The release of the active agent(s) can be constant over a long or short period, it can be cyclic over a long or short period, or it can be triggered by the environment or other external events (see, e.g., Langer and Tirrell, *Nature* 428:487-492, 2004). In general, controlled-release polymer systems can provide drug levels in a specific range over a longer period of time than other drug delivery methods, thus increasing the efficacy of the drug and maximizing patient compliance.

There are several different ways in which the nanoparticles can be formulated for controlled release. For example, the molecular weight of PLGA in PLGA-PEG present in a nanoparticle can be varied, the size of the nanoparticle can be varied, the ratio of lactic acid to glycolic acid in PLGA present in the nanoparticle can be varied, the molecular weight of the polymer containing a hydrophobic polymer that is linked to a Pt-containing chemotherapeutic drug can be varied, and the amount of Pt-containing chemotherapeutic drug incorporated in the nanoparticle in order to affect the controlled release of the Pt-containing chemotherapeutic agent and the topoisomerase inhibitor from the nanoparticle. These and additional examples of methods of formulating a nanoparticle for controlled release are described in Fredenberg et al., *Int. J. Pharmaceut.* 415:34-52, 2011.

Formulations and Compositions

In some embodiments, the nanoparticles are combined with a pharmaceutically acceptable excipient to form a pharmaceutical composition. As would be appreciated by one of skill in this art, the excipient can be chosen based on the particular route of administration, the location of the target issue, the composition being delivered, and the desired time course of delivery of the composition.

In some embodiments, the composition contains a therapeutically effective amount of the nanoparticles formulated together with one or more pharmaceutically acceptable excipients. As described in detail, the compositions of the present invention can be specially formulated for administration in solid or liquid form, including those adapted for the following: oral administration, for example, drenches (aqueous or non-aqueous solutions or suspensions), tablets. e.g., those targeted for buccal, sublingual, and systemic absorption, boluses, powders, granules, pastes for application to the tongue; parenteral administration, for example, by subcutaneous, intramuscular, intravenous, or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary, and to other mucosal surfaces.

A pharmaceutically acceptable excipient can be solid or a vehicle, such as a liquid or solid filler, diluent, or solvent material, that can carry or transport a nanoparticle from one organ, or portion of the body, to another organ, or portion of the body. Each excipient should be compatible with the other ingredients of the composition and not injurious to the patient. Some examples of materials which can serve as pharmaceutically acceptable excipients include without limitation: sugars, such as lactose, glucose and sucrose; starches, such as corn starch and potato starch; cellulose, and its derivatives, such as sodium carboxymethyl cellulose, ethyl cellulose, and cellulose acetate; powdered tragacanth; malt; gelatin; talc; cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH-buffered solutions; polyesters, polycarbonates, and/or polyanhydrides; and other non-toxic compatible substances employed in pharmaceutical formulations.

The compositions can also contain a wetting agent, an emulsifier, and a lubricant, such as sodium lauryl sulfate and magnesium stearate, as well as coloring agents, release agents, coating agents, sweetening, flavoring, and perfuming agents, preservatives, and antioxidants. Non-limiting examples of pharmaceutically-acceptable antioxidants that can be included in any of the compositions described herein include: water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol (e.g., alpha-tocopheryl succinate), and the like; and metal chelating agents, such as citric acid, ethylenediamine tetraacetic acid (EDTA), sorbitol, tartaric acid, phosphoric acid, and the like.

The compositions of the present invention can be formulated in dosages, generally, at the maximum amount while avoiding or minimizing any potentially detrimental side effects. The compositions can be administered in effective amounts, alone or in a cocktail with one or more additional anti-cancer agents (e.g., any of the exemplary anti-cancer agents described herein or known in the art). An effective amount is generally an amount sufficient to decrease cancer cell proliferation (e.g., in a human subject), induce cancer cell death (e.g., in a human subject), or treat cancer in a subject (e.g., a human).

One of skill in the art can determine what an effective dosage of the composition is by screening the composition using any of the assays described herein or other known assays. The effective amount may depend, of course, on factors such as the stage of the cancer being treated, individual patient parameters including age, physical condition, sex, size, and mass, concurrent anti-cancer treatments, the rate of excretion or metabolism of the composition being employed, the duration of the treatment, the time of administration, the frequency of treatment, the activity of the particular composition, the mode of administration, prior medical history of the subject being treated, and like factors well known in the medical arts. These factors are well known to those of ordinary skill in the art and can be addressed with no more than routine experimentation. In some cases, a maximum dosage be used, that is, the highest safe dosage according to sound medical judgment.

Actual dosage levels of the active agents (e.g., Pt-containing chemotherapeutic agent and the topoisomerase inhibitor) in the compositions provided herein can be varied so as to obtain an amount of the active agents that is effective to achieve the desired therapeutic response for a particular subject and mode of administration, without being toxic to the subject. In some embodiments, the composition (e.g., any of the compositions described herein) is formulated in a single dose of between 1 mg to 500 mg (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg).

Devices

In some embodiments, the compositions (e.g., any of the compositions described herein) can be provided in an ampule or a preloaded syringe. In some embodiments, the ampule or preloaded syringe contains a single dosage of a composition.

In some embodiments, the compositions (e.g., any of the compositions described herein) are provided (e.g., in a kit) with instructions that describe any of the methods described herein. In some embodiments, the compositions are provided in a kit with instructions to administer the composition to a subject having cancer.

Methods of Making Nanoparticles

Also provided herein are methods of making the nanoparticles described herein. These methods include mixing (i) a plurality polymers, wherein at least a fraction of the polymers contain a hydrophobic polymer linked to a Pt-containing chemotherapeutic agent, and (ii) a topoisomerase inhibitor in an organic solvent to form an organic precursor solution; and contacting the organic precursor solution with an aqueous solvent to achieve a ratio of about 5:1 to about 20:1 (e.g., about 5:1 to about 15:1 or about 5:1 to about 10:1), wherein the contacting results in the self-assembly of a nanoparticle. In some embodiments, the plurality of polymers further contains at least one polymer linked to a targeting moiety. In some embodiments, the topoisomerase inhibitor is linked to at least one polymer. Some embodiments further include a step of adding a layer of surfactant to the outer surface of the nanoparticle.

In some embodiments, the ratio of polymers containing a hydrophobic polymer linked to a targeting moiety, polymers containing a hydrophobic moiety linked to a Pt-containing chemotherapeutic agent, and polymers containing a hydrophobic moiety that are not linked to a targeting moiety, a Pt-containing chemotherapeutic agent, or a topoisomerase inhibitor in the organic precursor solution is about 1:2:1. In some embodiments, the total polymer concentration in the organic precursor solution is between 5 mg/mL to 15 mg/mL, 6 mg/mL to 14 mg/mL, 7 mg/mL to 13 mg/mL, 8 mg/mL to 12 mg/mL, or 9 mg/mL to 11 mg/mL. In some embodiments, the concentration of topoisomerase inhibitor (e.g., irinotecan) in the organic precursor solution is sufficient to achieve a final drug loading of 5%. In some embodiments, the topoisomerase inhibitor is linked to at least one polymer containing a hydrophobic polymer.

In some embodiments, the organic solvent contains acetonitrile. In some embodiments, the organic solvent contains acetonitrile, ethyl acetate, tetrahydrofuran, dichloromethane, acetone, dimethylformamide, and/or dimethyl sulfoxide.

In some embodiments, the mixing is performed at a temperature of between 20° C. to 30° C., between 22° C. to 28° C., or between 24° C. to 26° C. In some embodiments, the mixing is performed by convection. In some embodiments, the mixing is performed by physical agitation of the precursor organic solution. In some embodiments, the mixing is performed for at least 1 minute (e.g., at least 5, 10, 20, 30, 40, or 50 minutes). In some embodiments, the mixing is performed between 1 to 360 minutes, 60 to 240 minutes, or 120 to 180 minutes. In some embodiments, the contacting is performed at a temperature of between 20° C. to 30° C., between 22° C. to 28° C., or between 24° C. to 26° C.

In some embodiments, the contacting is performed by passing the organic precursor solution through a microfluidic device. Microfluidic devices enable the rapid contacting of the organic precursor solution with an aqueous solution (e.g., water) and result in the nanoprecipitation of nanoparticles. The ability to controllably and rapidly mix reagents and provide homogeneous reaction environments make microfluidic devices ideally suited for the synthesis of monodispersed nanoparticles (DeMello and DeMello, *Lab on a Chip* 4:11N-15N, 2004). The use of microfluidic devices can provide dramatic enhancement in the homogeneity of the resulting nanoparticles and a significant improvement in the reproducibility as compared to conventional nanoprecipitation without control over the mixing time.

In some embodiments, the microfluidic device is made of polydimethylsiloxane (PDMS) (see, e.g., Karnik et al., *Nano Lett.* 8:2906-2912, 2008, and Valencia et al., *ACS Nano* 4:1671-1679, 2010). In some embodiments, the microfluidic device contains a mixing channel that is ~20 μm wide, ~60 μm high, and ~1 cm long. In some embodiments, the microfluidic device performs hydrodynamic flow focusing. In some embodiments, the organic precursor solution is passed through the microfluidic device at a rate of between 3 μL/minute to 100 μL/minute (e.g., between 3 μL/minute to 80 μL/minute, between 3 μL/minute and 60 μL/minute, between 3 μL/minute and 40 μL/minute, between 3 μL/minute and 30 μL/minute, between 3 μL/minute and 20 μL/minute, between 3 μL/minute to 12 μL/minute, between 3 μL/minute to 10 μL/minute, or between 3 μL/minute to 7 μL/minute). In some embodiments, the aqueous solution is passed through the microfluidic device at a rate of between 3 μL/minute to 500 μL/minute (e.g., between 3 μL/minute to 400 μL/minute, 3 μL/minute to 300 μL/minute, 3 μL/minute to 200 μL/minute, 3 μL/minute to 100 μL/minute, 3 μL/minute to 50 μL/minute, 3 μL/minute to 15 μL/minute, between 3 μL/minute to 10 μL/minute, or between 3 μL/minute to 7 μL/minute). In some embodiments, the aqueous solution is passed through the microfluidic device at a rate that is between 5- to 20-fold (e.g., 10- to 16-fold or 12- to 14-fold) faster than the rate that the organic precursor solution is passed through the microfluidic device.

In some embodiments, the passing is performed at a temperature of between 20° C. and 30° C. (e.g., between 22° C. and 28° C., between 23° C. and 26° C., and between 24° C. and 25° C.). These methods can also be performed using a chaotic advection mixer (e.g., Herringbone mixer), a zigzag mixer, a droplet mixer, a shear superposition mixer, a T-mixer, a mixer based on Tesla microstructures, or an active mixer. Additional examples of mixing techniques are described in Nguyen et al., *J. Micromechan. Microeng.* 15:R1, 2005.

Some embodiments of these methods further include washing the nanoparticles in an aqueous solvent (e.g., water). In some embodiments, the washing can be performed using a filtration membrane (e.g., an Amicon centrifugation filtration membrane).

In some embodiments, the resulting nanoparticle has a diameter of between 40 nm to 80 nm (e.g., between 45 nm to 75 nm, between 50 nm to 70 nm, and between 55 nm to 65 nm). In some embodiments, the resulting nanoparticle contains any of the polymers containing a hydrophobic polymer linked to a targeting moiety described herein. In some embodiments, a polymer that contains a hydrophobic polymer that is linked to a targeting moiety is PLGA-PEG. In some embodiments, the targeting moiety is a nucleic acid (e.g., a nucleic acid comprising at least one nucleoside analogue or at least one modification in the polyphosphate backbone), a small molecule (e.g., a carbohydrate or hydrocarbon), a polypeptide, or an aptamer. In some embodiments, the small molecule is S,S-2[3-][5-amino-1-carboxypentyl]-ureido]-pentanedioic acid (LIG). In some embodiments, a polymer containing a hydrophobic polymer linked to a targeting moiety is PLGA-PEG-LIG.

In some embodiments, the polymer containing a hydrophobic polymer linked to a Pt-containing chemotherapeutic agent contains a polylactic acid, a polycaprolactone, or a polyanhydride. In some embodiments, the polymer containing a hydrophobic polymer linked to a Pt-containing chemotherapeutic agent contains a polylactic acid. In some embodiments, the Pt-containing chemotherapeutic agent is selected from the group of: cisplatin, carboplatin, oxaliplatin, satraplatin, picoplatin, and aroplatin. In some embodiments, the polymer containing a hydrophobic polymer linked to a Pt-containing chemotherapeutic agent is PLA-cisplatin. In some embodiments, the Pt-containing chemotherapeutic agent is linked to the polymer containing a hydrophobic polymer through an ester, an amide, or an ether bond.

In some embodiments, the plurality of polymers containing a hydrophobic polymer comprises a PLGA-PEG. In some embodiments, the topoisomerase inhibitor is selected from the group consisting of: irinotecan, SN-38, topotecan, and camptothecin.

In some embodiments, the plurality of polymers includes PLGA-PEG-LIG and PLA-cisplatin, and the topoisomerase inhibitor is irinotecan. In some embodiments, the nanoparticle contains the topoisomerase inhibitor and the Pt-containing chemotherapeutic agent in a ratio of about 24:1 to 1:24 (e.g., ~4:1, 3.5:1, 2:1, 1:2, 1:3.5, or 1:4). In some embodiments, the topoisomerase inhibitor is linked to at least one polymer containing a hydrophobic polymer.

Methods of Inhibiting or Reducing Cancer Cell Proliferation

Also provided are methods of reducing the proliferation of a cancer cell that include contacting a cancer cell with an amount of any of the compositions described herein sufficient to reduce the proliferation of the cancer cell. In some embodiments, the amount of the composition is sufficient to induce death of the cancer cell.

In some non-limiting embodiments, the composition contains nanoparticles containing: PLGA-PEG-LIG, PLA-cisplatin, PLGA-PEG, and irinotecan. In some embodiments, the composition contains nanoparticles containing PLGA-PEG-LIG, PLA-cisplatin, PLGA-PEG, and irinotecan, where the irinotecan and cisplatin are present in a ratio of about 24:1 to about 1:24 (e.g., 4:1 to 1:4, about 2, or about 3.5). In some embodiments, the composition contains nanoparticles containing PLGA-PEG-LIG, PLA-cisplatin, PLA-irinotecan, and PLGA-PEG.

In some embodiments, the cancer cell is selected from the group of: a breast cancer cell, a colon cancer cell, a leukemia cell, a bone cancer cell, a lung cancer cell, a bladder cancer cell, a brain cancer cell, a bronchial cancer cell, a cervical cancer cell, a colorectal cancer cell, an endometrial cancer cell, an ependymoma cancer cell, a retinoblastoma cancer cell, a gallbladder cancer cell, a gastric cancer cell, a gastrointestinal cancer cell, a glioma cancer cell, a head and neck cancer cell, a heart cancer cell, a liver cancer cell, a pancreatic cancer cell, a melanoma cancer cell, a kidney cancer cell, a laryngeal cancer cell, a lip or oral cancer cell, a lymphoma cancer cell, a mesothioma cancer cell, a mouth cancer cell, a myeloma cancer cell, a nasopharyngeal cancer cell, a neuroblastoma cancer cell, an oropharyngeal cancer cell, an ovarian cancer cell, a thyroid cancer cell, a penile cancer cell, a pituitary cancer cell a prostate cancer cell, a rectal cancer cell, a renal cancer cell, a salivary gland cancer cell, a sarcoma cancer cell, a skin cancer cell, a stomach cancer cell, a testicular cancer cell, a throat cancer cell, a uterine cancer cell, a vaginal cancer cell, and a vulvar cancer cell.

In some embodiments, the cancer cell is present in vivo. In some embodiments, the cancer cell is an ex vivo culture. In some embodiments, the cancer cell is grown in a tissue culture medium.

In some embodiments, the cancer cell is present in a mammal (e.g., a human or domesticated animal, such as a dog, cat, mouse, rat, rabbit, horse, monkey, cow, or pig). In some embodiments, the mammal (e.g., human) has been previously diagnosed as having a cancer (e.g., any of the forms of cancer described herein). In some embodiments, the subject is a female. In some embodiments, the subject is a male. In some embodiments, the subject has been previously treated with another anti-cancer agent. In some embodiments, the subject has previously responded poorly to another anti-cancer agent. In some embodiments, the subject may have inoperable cancer. In some embodiments, the subject is a child. In some embodiments, the subject is an adult (e.g., between 18 to 20 years old or at least 20, 25, 30, 35, 40, 45, 50, 55, 60, 65, 70, 75, 80, 85, 90, 95, or 100 years old).

In some embodiments, the composition is administered by intravenous, intraarterial, subcutaneous, intraperitoneal, intramuscular, ocular, or intrathecal administration. In some embodiments, the composition is administered by local administration to a tissue within the mammal containing the cancer cell.

In some embodiments, the composition is administered by a medical professional (e.g., a physician, a physician's assistant, a nurse, a nurse's assistant, or a laboratory technician) or veterinary professional. In some embodiments, the composition is self-administered by the subject. The composition can be administered in a hospital, a clinic, or a primary care facility (e.g., a nursing home).

The appropriate amount (dosage) of the composition administered can be determined by a medical professional or a veterinary professional based on a number of factors including, but not limited to, the type of cancer cell, the route of administration of the composition, the location of the cancer cell (in a subject), the severity or stage of cancer (in a subject diagnosed with cancer), the subject's responsiveness to other anti-cancer agents, the health of the subject, the subject's mass, the other therapies administered to the subject, the age of the subject, the sex of the subject, and any other co-morbidity present in the subject.

A medical professional or veterinary professional having ordinary skill in the art can readily determine the effective amount of the composition that is required. For example, a physician or veterinarian could start with doses of the composition (e.g., any of the compositions described herein) at levels lower than that required to achieve the desired therapeutic effect and then gradually increasing the dose until the desired effect is achieved.

In some embodiments, the subject is administered a dose of between 1 mg to 500 mg of any of the compositions described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). The amount of the composition administered will depend on whether the composition is administered locally or systemically. In some embodiments, the subject is administered more than one dose of the composition. In some embodiments, the subject is administered a dose of the composition at least once a month (e.g., at least twice a month, at least three times a month, at least four times a month, at least once a week, at least twice a week, three times a week, once a day, or twice a day).

In some embodiments, the composition is provided to a subject chronically. Chronic treatments include any form of repeated administration for an extended period of time, such as repeated administrations for one or more months, between a month and a year, one or more years, or longer.

In some embodiments, chronic treatments can involve regular administrations, for example one or more times a day, one or more times a week, or one or more times a month. In general, a suitable dose such as a daily dose of the compound will be the amount of the compound that is the lowest dose effective to produce a desired therapeutic effect. Such an effective dose will generally depend upon the factors described herein. If desired, the effective daily dose of the compound can be administered as two, three, four, five, or six or more sub-doses administered separately at appropriate intervals throughout the day, optionally, in unit dosage forms.

Some embodiments further include contacting the cancer cell with one or more additional anti-cancer agents selected from the group: an alkylating agent (e.g., any of the alkylating agents described herein or known in the art), an antimetabolite (e.g., any of the antimetabolites described herein or known in the art), an anthracycline (e.g., any of the anthracyclines described herein or known in the art), a plant alkyloid (e.g., any of the plant alkyloids described herein or known in the art), and a therapeutic antibody or an antigen-binding antibody fragment that specifically binds to a tumor antigen (e.g., any of the antibodies or antigen-binding antibody fragments described herein or known in the art). In some embodiments, the dose of an anti-cancer agent administered to a subject is between 1 mg to 500 mg of any of the additional anti-cancer agents described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). In some embodiments, the one or more additional anti-cancer agents are administered at least once a month (e.g., at least twice a month, at least three times a month, at least four times a month, at least once a week, at least twice a week, three times a week, once a day, or twice a day). In some embodiments, the one or more additional anti-cancer agents and any of the compositions described herein can be administered at substantially the same time to the subject.

A reduction in the proliferation of a cancer cell can be determined in vitro using a number of different methods for detecting the rate of cellular proliferation. For example, the proliferation of a cancer cell can be detected by microscopic techniques and cell counting (e.g., cell counting performed using fluorescence assisted cell sorting or a hemocytometer).

A reduction in the proliferation of a cancer cell in vivo (e.g., in a human) can be detected by medical imaging (e.g., magnetic resonance imaging, X-ray, ultrasound, positron emission tomography, and computed tomography) (i.e., a reduction in the rate of growth of a tumor in a subject). A reduction in the proliferation of a cancer cell can also be assessed by a decrease in the number of symptoms of cancer in a subject, a decrease in the rate of development of symptoms of cancer in the subject, or a decrease in the frequency, intensity, and/or duration or one of more symptoms of cancer in a subject.

Methods of Treating Cancer in a Subject

Also provided are methods of treating a cancer in a subject that include administering an amount of any of the compositions described herein sufficient to treat a cancer in a mammal. In some embodiments, the composition contains nanoparticles containing PLGA-PEG-LIG, PLA-cisplatin, PLGA-PEG, and irinotecan. In some embodiments, the composition contains nanoparticles containing PLGA-PEG-LIG, PLA-cisplatin, PLGA-PEG, and irinotecan, where irinotecan and cisplatin are present in a ratio of about 24:1 to about 1:24 (e.g., about 4:1 to about 1:4). In some embodiments, the composition contains nanoparticles containing PLGA-PEG-LIG, PLA-cisplatin, PLA-irinotecan, and PLGA-PEG.

In some embodiments, the mammal (e.g., human) has been previously diagnosed as having a cancer. In some embodiments, the cancer is a metastatic cancer. In some embodiments, the cancer is selected from the group of: breast cancer, colon cancer, leukemia, bone cancer, lung cancer, bladder cancer, brain cancer, bronchial cancer, cervical cancer, colorectal cancer, endometrial cancer, ependymoma, retinoblastoma, gallbladder cancer, gastric cancer, gastrointestinal cancer, glioma, head and neck cancer, heart cancer, liver cancer, pancreatic cancer, melanoma, kidney cancer, laryngeal cancer, lip or oral cancer, lymphoma, mesothioma, mouth cancer, myeloma, nasopharyngeal cancer, neuroblastoma, oropharyngeal cancer, ovarian cancer, thyroid cancer, penile cancer, pituitary cancer, prostate cancer, rectal cancer, renal cancer, salivary gland cancer, sarcoma, skin cancer, stomach cancer, testicular cancer, throat cancer, uterine cancer, vaginal cancer, and vulvar cancer.

A subject can be diagnosed as having cancer based on the detection of one or more symptoms of a cancer in a subject. The specific symptoms of a cancer will depend on the particular type of cancer. Non-limiting symptoms of cancer include: fatigue, a lump or thickening that can be felt under the skin, weight changes (unintended weight loss or gain), skin changes (e.g., yellowing, darkening, or redness of the skin, or sores), fever, changes in bowel or bladder habits, persistent cough, difficulty swallowing, hoarseness, persistent indigestion or discomfort after eating, persistent, unexplained muscle or joint pain. Symptoms of prostate cancer include burning or pain during urination, inability to urinate, frequent nocturnal urination, weak urine stream, and blood in urine. A subject can also be determined to have cancer based on the outcome of a molecular diagnostic test (e.g., Her2/Neu screening and prostate specific membrane antigen screening). A subject can also be determined to have cancer based on the results of a biopsy.

In some embodiments, an effective treatment of a cancer will result in a decrease in the spread of a cancer to secondary sites in the body (a decrease in the rate of metastasis), a decrease in the proliferation of cancer cells in a subject (e.g., a decrease in the rate of growth of a tumor in a subject), a decrease in the number of symptoms of a cancer in a subject, a decrease in the rate of development of symptoms of cancer in a subject, a decrease in the frequency, severity, or duration of one or more symptoms of cancer in a subject, and/or an increase in the length of remission in a subject. The efficacy of treatment of a cancer can be determined using methods known in the art. A medical professional or a veterinary profession can readily determine the efficacy of treatment of a cancer in a subject.

In some embodiments, the subject is a female. In some embodiments, the subject is a male. In some embodiments, the subject can have a severe or advanced stage of cancer. In some embodiments, the subject can be in an early stage of cancer. In some embodiments, the subject may have been previously treated with another anti-cancer agent. In some embodiments, the subject has previously responded poorly to another anti-cancer agent. In some embodiments, the subject may have inoperable cancer. In some embodiments, the subject is a child. In some embodiments, the subject is an adult (e.g., between 18 to 20 years old or at least 20, 25, 30, 35, 40, 45, 50, 55, 60, 65, 70, 75, 80, 85, 90, 95, or 100 years old).

In some embodiments, the composition is administered by intravenous, intraarterial, subcutaneous, intraperitoneal, intramuscular, ocular, or intrathecal administration. In some embodiments, the composition is administered by local administration to a tissue within the mammal containing the cancer cell.

In some embodiments, the composition is administered by a medical professional (e.g., a physician, a physician's assistant, a nurse, a nurse's assistant, or a laboratory technician) or veterinary professional. In some embodiments, the composition is self-administered by the subject (e.g., by self-injection). The composition can be administered in a hospital, a clinic, or a primary care facility (e.g., a nursing home). In some embodiments, the composition is administered by infusion over a period of time (e.g., at least 5 minutes, 10 minutes, 15 minutes, 30 minutes, or 1 hour).

The appropriate amount (dosage) of the composition administered can be determined by a medical professional or a veterinary professional based on a number of factors including, but not limited to, the type of cancer, the route of administration of the composition, the location of the cancer cell in the subject, the severity or stage of cancer, the subject's responsiveness to other anti-cancer agents, the health of the subject, the subject's mass, the other therapies administered to the subject, the age of the subject, the sex of the subject, and any other co-morbidity present in the subject.

A medical professional or veterinary professional having ordinary skill in the art can readily determine the effective amount of the composition that is required. For example, a physician or veterinarian could start with doses the composition (e.g., any of the compositions described herein) at levels lower than that required to achieve the desired therapeutic effect and then gradually increasing the dose until the desired effect is achieved.

In some embodiments, the subject is administered a dose of between 1 mg to 500 mg of any of the compositions described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). In other examples, the subject is administered a dose of between about 1 mg total polymer/kg to about 6000 mg total polymer/kg (e.g., between about 10 mg total between about 10 mg total polymer/kg to about 5000 mg total polymer/kg, between about 10 mg total polymer/kg to about 4000 mg total polymer/kg, between about 10 mg total polymer kg to about 3000 mg total polymer/kg, between about 10 mg total polymer/kg to about 2000 mg total polymer/kg, or between about 10 mg total polymer/kg to about 1000 mg total polymer/kg). The amount of the composition administered will depend on whether the composition is administered locally or systemically (e.g., intravenously). In some embodiments, the subject is administered more than one dose of the composition. In some embodiments, the subject is administered a dose of the composition at least once a month (e.g., at least twice a month, at least three times a month, at least four times a month, at least once a week, at least twice a week, three times a week, once a day, or twice a day).

In some embodiments, the composition is provided to a subject chronically. Chronic treatments include any form of repeated administration for an extended period of time, such as repeated administrations for one or more months, between a month and a year, one or more years, or longer. In some embodiments, chronic treatments can involve regular administrations, for example one or more times a day, one or more times a week, or one or more times a month. In general, a suitable dose such as a daily dose of the compound will be the amount of the compound that is the lowest dose effective to produce a desired therapeutic effect. Such an effective dose will generally depend upon the factors described herein. If desired, the effective daily dose of the compound can be administered as two, three, four, five, or six or more sub-doses administered separately at appropriate intervals throughout the day, optionally, in unit dosage forms.

Some embodiments further include administering to the subject one or more additional anti-cancer agents selected from the group: an alkylating agent (e.g., any of the alkylating agents described herein or known in the art), an antimetabolite (e.g., any of the antimetabolites described herein or known in the art), an anthracycline (e.g., any of the anthracyclines described herein or known in the art), a plant alkyloid (e.g., any of the plant alkyloids described herein or known in the art), and a therapeutic antibody or an antigen-binding antibody fragment that specifically binds to a tumor antigen (e.g., any of the antibodies or antigen-binding fragments described herein or known in the art). In some embodiments, the one or more additional cancer therapeutics are selected from the group consisting of: cyclophosphamide, methotrexate, 5-fluorouracil, doxorubicin, paclitaxel, doxorubicin, epirubicin, trastuzumab, lapatinib, bevacizumab, abraxane, pamidronate, anastrozole, exemestane, fulvestrant, letrozole, gemcitabine, pegfilgrastim, filgrastin, doxetaxel, capecitabine, goserelin, zoledronic acid, and ixabepilone.

In some embodiments, the dose of an additional anti-cancer agent administered to a subject is between 1 mg to 500 mg of any of the additional anti-cancer agents described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). In some embodiments, the one or more additional anti-cancer agents are administered at least once a month (e.g., at least twice a month, at least three times a month, at least four times a month, at least once a week, at least twice a week, three times a week, once a day, or twice a day). In some embodiments, the composition contains one or more additional anti-cancer agents and nanoparticles (e.g., any of the nanoparticles described herein). In some embodiments, the one or more additional anti-cancer agents and any of the compositions described herein can be administered at substantially the same time to the subject.

The invention is further described in the following example, which does not limit the scope of the invention described in the claims.

EXAMPLES

Example 1. Prostate Specific Membrane Antigen (PMSA)-Targeted Nanoparticles Containing Unconjugated Irinotecan and Use of the Nanoparticles to Mediate Prostate Cancer Cell Death PMSA-targeted nanoparticles were produced that contain the combination of a Pt-containing chemotherapeutic agent and an unconjugated topoisomerase inhibitor. The cytotoxic effect of these nanoparticles was tested using a prostate cancer cell line. The materials and methods used to perform these experiments are described below.

Materials and Methods
Materials
Poly(D,L-lactide-co-glycolide)-co-poly(ethylene glycol) with terminal methoxy groups (PLGA27K-mPEG5K) was obtained from Boehringer Ingelheim (Ingelheim am Rhein, Germany). Poly(D,L-lactide-co-glycolide) (50/50) with terminal carboxylate groups (PLGA, inherent viscosity 0.67 dL/g, MW~45 kDa) was obtained from Lactel (Pelham, Ala.). tBOC-NH-PEG-NH$_2$ (MW 5000) and tBOC-NH-PEG-NHS (MW 5000) were purchased from Laysan Bio, Inc (Arab, Ala.). 3-(4,5-Dimethylthiazol-2-yl)-2,5-diphenyl tetrazolium bromide (MTT) reagent was purchased from Sigma-Aldrich (St. Louis, Mo., USA). Molecular biology buffers and tissue culture reagents were purchased from Invitrogen (Carlsbad, Calif.). The LNCaP cell line was obtained from American Type Culture Collection (Manassas, Va.).

Synthesis of PLGA-PEG-LIG
The synthesis of PLGA$_{45K}$-PEG$_{5K}$-LIG was accomplished first by the conjugation of LIG to PEG, followed by the conjugation of the resultant LIG-PEG to PLGA. First, LIG (3.9 mg, 8.9 µmol) was dissolved in 400 µL of dimethylformamide (DMF) and reacted with tBOC-NH-PEG-NHS (22 mg, 4.5 µmol) and N,N-diisopropylethylamine (DIEA, 10 µL) for 12 hours. The reaction product was dialyzed 24 hours in water to remove any unreacted LIG. The resultant tBOC-PEG-LIG was lyophilized and reconstituted in 400 µL of trifluoroacetic acid (TFA) to remove the protecting group. After 4 hours of reaction, the product was dried under vacuum and dissolved in 200 µL of dimethyl sulfoxide (DMSO). Concurrently, PLGA-COOH (100 mg, 2.2 µmoL) was reacted with N-hydroxysuccinimide (NHS) in the presence of 1-ethyl-3-[3-dimethylaminopropyl]carbodiimide (EDC) in dichloromethane (DCM) for 2 hours. PLGA-NHS was dried under vacuum and dissolved in 300 µL of DMSO. Finally, PEG-LIG and PLGA-NHS in DMSO were mixed with diisopropylethylamine (DIEA), allowed to react for 24 hours, precipitated in ice cold methanol, and dried under vacuum. PLGA-PEG-LIG was characterized with gel permeation chromatography (GPC) to confirm the presence of the triblock PLGA-PEG-LIG.

Synthesis of PLA-Cisplatin
The synthesis of PLA-cisplatin was accomplished as described previously (Kolishetti et al., *Proc. Natl. Acad. Sci. U.S.A.* 107:17939-17944, 2010). The first step involved the preparation of functionalized lactic acid monomer, by conversion of the amine to a hydroxyl group via diazotization using sodium nitrite in the presence of an acid for 6 hours. This reaction provided the resultant monomer for direct use in condensation polymerization with lactic acid to give a polylactide copolymer, PLA-OBn. The condensation polymerization was then performed at 150° C. for 3 hours with a continuous argon purge, followed by a further 3 hours under vacuum. The same polymer was prepared using a ring-opening polymerization the cyclic lactide monomer and functionalized cyclic lactide monomer. The functionalized cyclic lactide monomer was made by dehydration of the α-hydroxyl acid under very dilute conditions in toluene with 1% p-toluenesulfonic acid. The hydroxyl-functionalized biodegradable polylactide (PLA-OH) was obtained by benzyl deprotection using a Pd/C catalyst at 50 psi pressure for 8 hours. Finally, succinic acid derivatized platinum (IV) (cisplatin prodrug) was linked with the PLA-OH using dicyclohexylcarbodiimide (DCC)/hydroxybenzotriazole coupling for 12 hours in dimethylformamide at room temperature to produce PLA-cisplatin.

Synthesis and Characterization of Nanoparticles

Nanoparticle synthesis was carried out in microfluidic devices made of polydimethylsiloxane (PDMS) as previously described in Karnik et al. (*Nano Lett.* 8:2906-2912, 2008) and Valencia et al. (*ACS Nano* 4:1671-1679, 2010). The device had one inlet each for water and precursors streams, and one outlet. The water stream was split into two in order to achieve two water streams at the flow focusing junction. The mixing channel was 20 µm wide, 60 µm high, and 1 cm long, 2.5-mL and 0.5-mL gas-tight syringes were used for aqueous and organic streams, respectively, and were mounted on a syringe pumps to control flow through the device. Nanoparticles were prepared by the nanoprecipitation method. In brief, PLGA-PEG was mixed with a pre-defined amount of PLGA-PEG-LIG and PLA-cisplatin in acetonitrile to yield a final polymer concentration of 10 mg/mL. Unconjugated irinotecan was mixed with the polymers to reach an initial drug loading of 5%. The organic stream (polymers, drugs, and acetonitrile) was run at 5 µL/minute, while the aqueous flow rate was maintained at 50 µL/minute. Nanoparticles were collected at the outlet stream, and washed three times with water using an Amicon centrifugation filtration membrane to remove excess drugs and organic solvents.

Particle sizing was performed using dynamic light scattering (DLS) with a Zetasizer Nano ZS instrument (Malvern Instruments Ltd., U.K.). For each measurement, 100 µL or more of the sample was loaded in a disposable low-volume cuvette. Transmission electron microscopy (TEM) experiments were carried out on a JEOL 2011 instrument at an acceleration voltage of 200 kV. The TEM sample was prepared by depositing 10 µL of the nanoparticle suspension (1.0 mg/mL) onto a 300-mesh carbon-coated copper grid. Samples were blotted away after 30 minutes incubation and the grids were negatively stained for 20 minutes at room temperature with a sterile-filtered 1% (w/v) uranyl acetate aqueous solution. Drug loading and encapsulation efficiency (EE) were determined by quantifying the amount of drug in the nanoparticles. Drug loading is defined as the mass fraction of the drug in the nanoparticles, whereas EE is the fraction of initial drug that is encapsulated by the nanoparticles. After synthesis, nanoparticles were dissolved in a solution 50/50 acetonitrile/water and vortexed for several hours to induce nanoparticle dissociation. The amount of platinum inside the nanoparticles was detected using Atomic Absorption Spectroscopy (AAS), from which the load of cisplatin was calculated. Irinotecan was detected using spectrophotometry on a TECAN 1000 plate reader at a wavelength of 385 nm. A calibration curve with known concentrations of irinotecan was prepared, and the amount of irinotecan encapsulated in the nanoparticles was calculated using the calibration curve.

Nanoparticle Binding and Uptake by LNCaP Cells

LNCaP cells were cultured in RPMI 1640 medium with 10% fetal bovine serum, 50 units/mL penicillin, and 50 mg/mL streptomycin. All cells were cultured at 37° C. and 5% $CO_2$. The cells were seeded at a density of 50,000 cells per well on a 24-well plate. After 24 hours, the cell medium was removed and replaced with nanoparticles dissolved in the same medium at a concentration of 1 mg/mL. Cells and nanoparticles were incubated for 4 hours followed by three washes with 1% bovine serum albumin (BSA) solution in phosphate buffered saline (PBS) to remove excess nanoparticles. LNCaP cells were treated with trypsin, removed from the plate, and centrifuged. The resulting cell pellets were reconstituted in 250 µL of PBS, and placed in a 96-well plate for fluorescence-assisted cell sorting (FACS) analysis. FACS analysis was performed on a BD Biosciences LSR II with High-Throughput Sampler (HTS) option, with 10.000 cells collected for each measurement. Four samples were analyzed per formulation (n=4).

In Vitro NP Cytotoxicity Assay

The cytotoxic behavior of all the nanoparticles was evaluated using a MTT assay. First cells were seeded on a 96-well plate in 100 µL of RPMI medium 1640, and incubated for 24 hours. Nanoparticles were freshly prepared in sterile PBS, and platinum and irinotecan content were quantified by AAS and spectrophotometry, respectively. The cells were then treated with different nanoparticles at varying concentrations, and incubated for 12 hours at 37° C. The medium was changed after 12 hours, and the cells were further incubated for another 48 hours. The cells were then treated with 20 µL of MTT (5 mg/mL in PBS), and incubated for 5 hours. The medium was removed, the cells were lysed by adding 100 µL of DMSO, and the absorbance of the purple formazan was recorded at 550 nm using a microplate reader. Each treatment was tested in triplicate in three independent experiments.

Results

Nanoparticles were produced that contain a PMSA-targeting moiety on their surface, and contain unconjugated irinotecan and conjugated cisplatin in their hydrophobic core. FIG. 1 is a schematic diagram showing these nanoparticles entering a cell and delivering irinotecan and cisplatin. The nanoparticles used in these experiments contain a PLGA core where both drugs are incorporated and a PEG shell decorated with LIG moieties that target PSMA. As the nanoparticles contact the cell surface, there are multivalent interactions between LIG and the extracellular domain of over-expressed PSMA receptors on the cell surface resulting in endocytosis of the nanoparticles (Chandran et al., *Cancer Biol. Ther.* 7:974-982, 2008). Once inside the cell, the nanoparticles release their dual cargo—irinotecan and cisplatin prodrug. Irinotecan is expected to be released at a faster rate than cisplatin, since the former is encapsulated inside the nanoparticle and can escape the core by diffusion, while the latter is linked to a polymer backbone which needs to be cleaved in order to become active. Once in the nucleus, irinotecan inhibits topoisomerase I, while cisplatin forms DNA adducts. The end result of both events is the signaling of cell replication arrest and apoptosis (Zastre et al., *Cancer Chemother. Pharmacol.* 60:91-102, 2007). The nanoparticles provide spatial control drug delivery, since both drugs will be released inside the cell, and temporal control by allowing one drug to be released at a different rate than the other.

Figure 2:
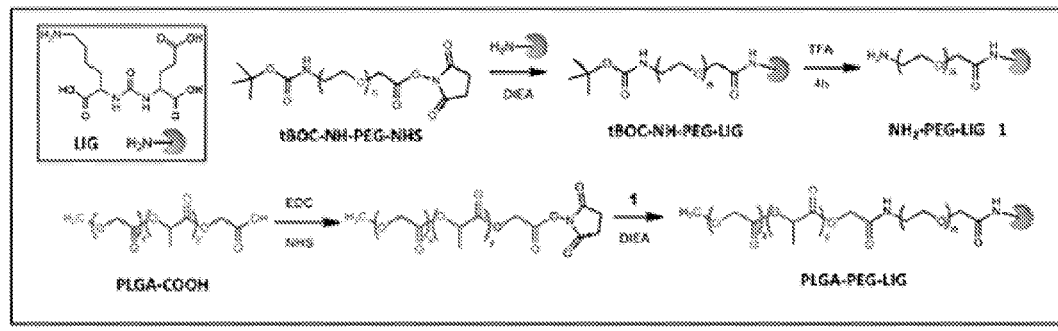
FIG. 2 is a schematic diagram of the synthesis of poly(lactide-co-glycolic acid)-polyethyleneglycol-S,S-2[3-][5-amino-1-carboxypentyl]-ureido]-pentanedioic acid (PLGA-PEG-LIG).

To minimize the number of steps in the preparation of targeted nanoparticles, a ligand-linked PLGA-PEG copolymer was synthesized (FIG. 2). LIG contains a free primary amine group that can be used to anchor LIG to the nanoparticle surface without affecting the targeting capabilities of the molecule. LIG was reacted with commercially-available succinimide-modified tBOC-NH-PEG-NHS, which after deprotection can be linked to a succinimide-modified PLGA. This functionalized polymer possessed all required components for a targeted nanoparticle and enabled single step self-assembly of targeted functional particles, simplifying the optimization and the potential scale-up.

Figure 3:
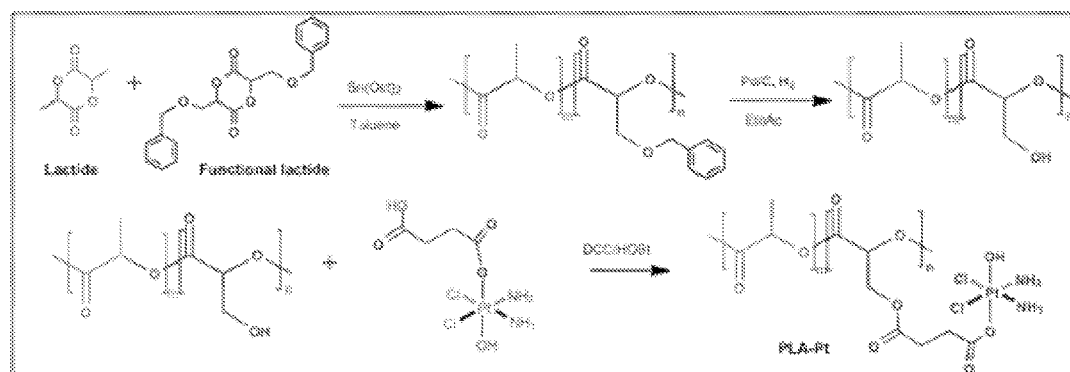
FIG. 3 is a schematic diagram of the synthesis of polylactic acid-cisplatin (PLA-cisplatin).

To co-deliver irinotecan and cisplatin, two therapeutic agents with varying physicochemical properties, a biodegradable polymer with reactive hydroxyl functional groups to enable the conjugation of a platinum prodrug to the polymer backbone was synthesized (FIG. 3). Previous work has demonstrated that this platinum prodrug can be cleaved from the backbone of the polymer and reduced to cisplatin once inside the cell leaving intact its capability of forming an adduct on DNA (Kolishetti et al., *Proc. Natl. Acad. Sci. U.S.A.* 107:17939-17944, 2010). Atomic absorption spectroscopy of PLA-cisplatin confirmed that ~2.5% of platinum was linked to the polymer.

Figures 4A, 4B, 4C, 4D:
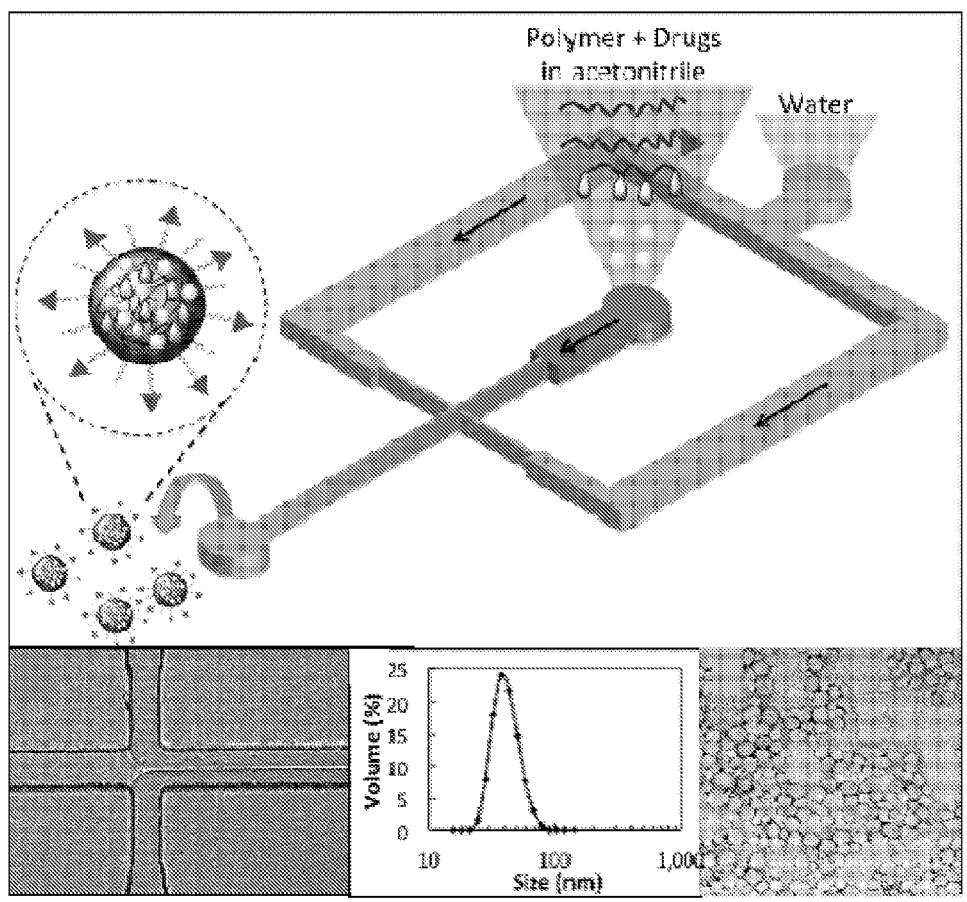
FIG. 4A is a schematic diagram of the synthesis of targeted nanoparticles in a microfluidic device using hydrodynamic flow focusing.
FIG. 4B is a photograph showing the flow focusing in a microfluidic channel during operation of a microfluidic device at an acetonitrile flow rate of 5 µL/minute and a water flow rate of 50 µL/minute.
FIG. 4C is a graph of the size distribution of targeted nanoparticles by volume. The average size of the nanoparticles is 55 nm, and the polydispersity index is 0.04.
FIG. 4D is a transmission electron micrograph of the nanoparticles stained with 1% solution of uranyl acetate. The average size of the nanoparticles is 55 nm.

The targeted nanoparticles used in these experiments are made of four different components that self-assemble in a single mixing step into a drug-loaded core-shell nanostructure decorated with targeting moieties on the surface. These components are: (1) PLGA-PEG core amphiphilic copolymer that forms the core-shell structure, (2) PLGA-PEG-LIG that self-assembles together with PLGA-PEG and orients LIG toward the NP surface, (3) PLA-cisplatin which assembles in the hydrophobic NP core by hydrophobic-hydrophobic interactions of PLGA and PLA, and (4) irinotecan, which partitions into the hydrophobic core based on its physicochemical properties. The nanoparticles were prepared in microfluidic channels through a rapid mixing strategy called hydrodynamic flow focusing (Karnik et al., *Nano Lett.* 8:2906-2912, 2008; and Rhee et al., *Adv. Mater.* 23:H79-H83, 2011) (FIG. 4A). In this method, polymers and drugs are mixed in acetonitrile and passed through a middle stream in a microfluidic device. The middle stream becomes horizontally focused into a very thin stream when it encounters two streams of water running a flow rate 10 times higher (FIG. 4B). Upon focusing, nanoprecipitation occurs through mixing of the aqueous and organic streams inducing nanoparticle self-assembly. This method ensures controlled precipitation and rapid mixing, which results in monodisperse nanoparticles with smaller size and higher drug loading than nanoparticles prepared through conventional bulk methods (Karnik et al., *Nano Lett.* 4:1671-1679, 2010). FIG. 4C shows the nanoparticle size distribution obtained by dynamic light scattering with an average of 55 nm and a polydispersity of 0.04 (indicative of monodisperse nanoparticles). Finally, a transmission electron micrograph of these nanoparticles shows an average size of ~55 nm which matches the value obtained using dynamic light scattering (FIG. 4D). The mixture of polymer precursors was composed of 25% PLGA-PEG-LIG, 50% PLA-cisplatin, and 25% PLGA-PEG. By assuming both an average nanoparticle density of 1.27 g/mL (Vauthier et al., *J. Nanoparticles Res.* 1:411-418, 1999) and that all PLGA-PEG-LIG self-assembles into a nanoparticle with all LIG molecules resulting on the nanoparticle surface (Valencia et al., *ACS Nano* 4:1671-1679, 2010), then nanoparticles with average diameter of 55 nm will have an average of 252 ligands per nanoparticle.

Figure 5:
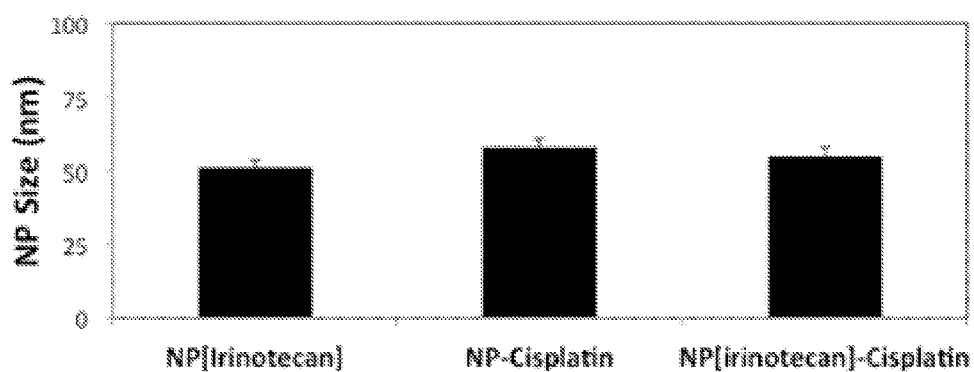
FIG. 5 is a graph of the average size of prostate-specific membrane antigen (PSMA)-targeted nanoparticles containing irinotecan (left column), PSMA-targeted nanoparticles containing cisplatin (center column), and PMSA-targeted nanoparticles containing both irinotecan and cisplatin (right column).
Figure 6:
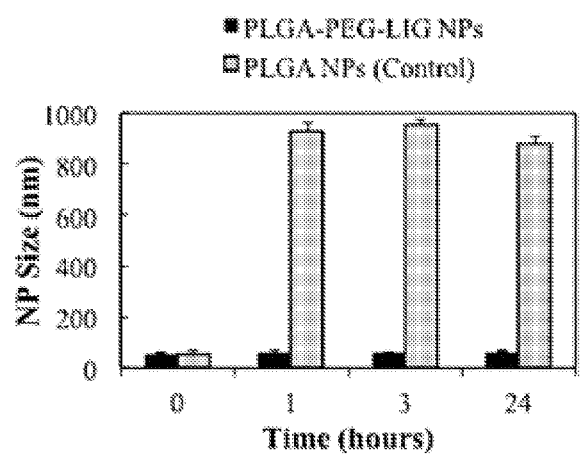
FIG. 6 is a graph of the size stability of PLGA-PEG-LIG nanoparticles and PLGA nanoparticles over time in 10% serum.

The size of nanoparticles encapsulating one or two drugs, as well as drug loading percentage and encapsulation efficiency of both drugs was evaluated to determine the effect of incorporating multiple drugs on the nanoparticles. FIG. 5 shows the size of nanoparticles encapsulating irinotecan (NP-IRN), cisplatin (NP-Pt), and both irinotecan and cisplatin (NP-IRN-Pt). Interestingly, the size of all three nanoparticles did not vary significantly, with each nanoparticle having an average diameter of approximately 55 nm. This is presumably due to the rapid mixing environment enabled by the microfluidic devices, which ensures complete mixing of precursors in water at a time scale smaller than the nanoparticle self-assembly, resulting in the formation of a uniform population of nanoparticles (Johnson et al., *Phys. Rev. Lett.* 91:118302, 2003). Furthermore, the size of the PLGA-PEG-LIG nanoparticles remained stable up to 24 hours (FIG. 6).

Figure 7:
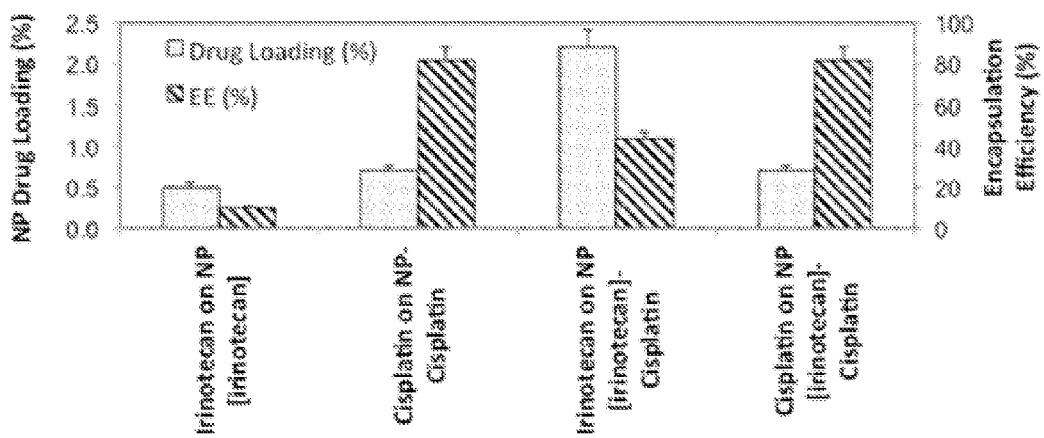
FIG. 7 is a graph showing the percentage drug loading and percentage encapsulating efficiency for a variety of nanoparticles containing either irinotecan (left set of columns) or cisplatin (center left set of columns), or both cisplatin and irinotecan (center right and right sets of columns). The left set and right center sets of columns show the percent of irinotecan loading and the irinotecan percentage encapsulation efficiency. The left center and left sets of columns show the percent of cisplatin loading and cisplatin percentage encapsulation efficiency.
Figure 8:
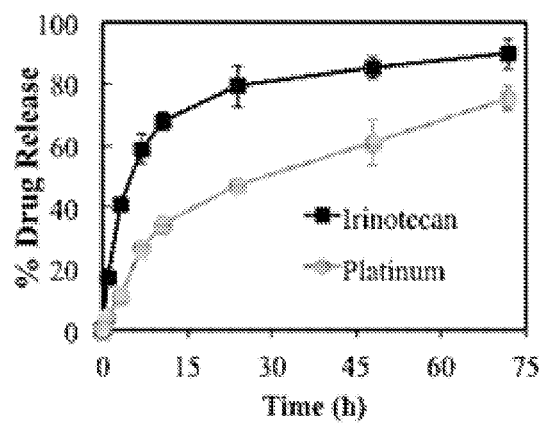
FIG. 8 is a graph showing the percent of irinotecan and platinum release from PLGA-PEG-LIG nanoparticles over time in phosphate buffered saline.

Next, the amount of cisplatin and irinotecan encapsulated in the nanoparticles as well their encapsulation efficiency (EE) was determined (FIG. 7). As expected, cisplatin was encapsulated with very high efficiency (>80%) due to the hydrophobic-hydrophobic interaction PLGA and PLA. Irinotecan, being a more hydrophilic molecule, exhibited an EE and drug loading of 10% and 0.5%, respectively, after self-assembly with PLGA-PEG. Interestingly, when irinotecan was mixed with both PLGA-PEG and PLA-cisplatin, its EE and drug loading increased to 44% and 2.2%, respectively. This might be due to hydrophilic-hydrophilic interactions of the platinum prodrug and irinotecan. This formulation resulted in an irinotecan to cisplatin ratio of 2:1, and these nanoparticles were used in the additional experiments described below. The percent drug release of irinotecan and platinum of these nanoparticles over time was also assessed. Irinotecan was released from these nanoparticles at a faster rate compared to the release of the Pt-containing chemotherapeutic agent (FIG. 8).

Figure 9:
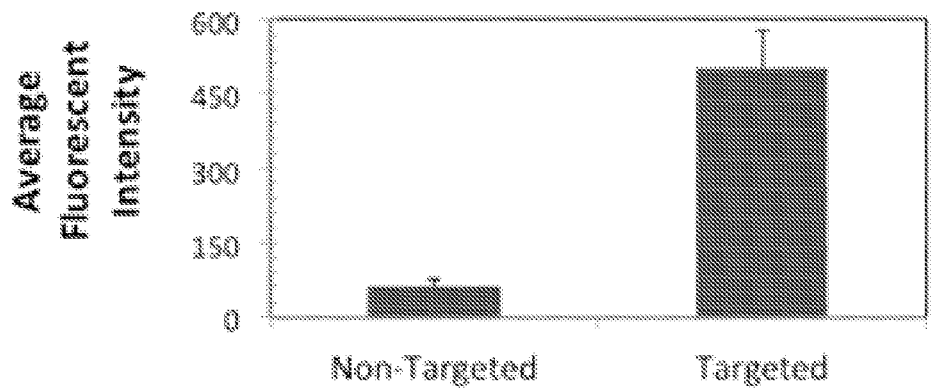
FIG. 9 is graph of fluorescence assisted cell sorting (FACS) data showing the average fluorescence of LNCaP cells treated with PSMA-targeted (right column) and PMSA-untargeted (left column) nanoparticles containing Alexa 488 linked to PLGA.
Figure 10A:
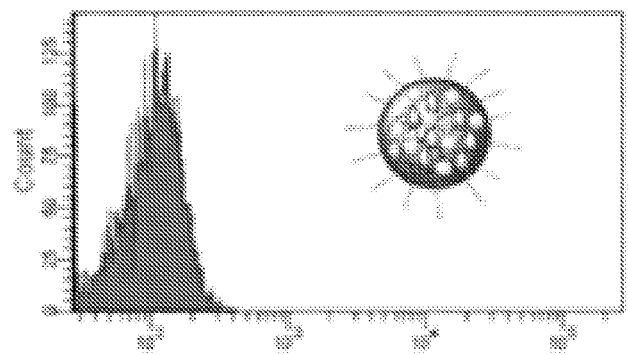
FIGS. 10A and 10B are two FACS histograms showing the fluorescence intensity of LNCaP cells treated with PMSA-untargeted (FIG. 10A) or PMSA-targeted (FIG. 10B) nanoparticles containing Alexa 488 linked to PLGA.
Figure 10B:
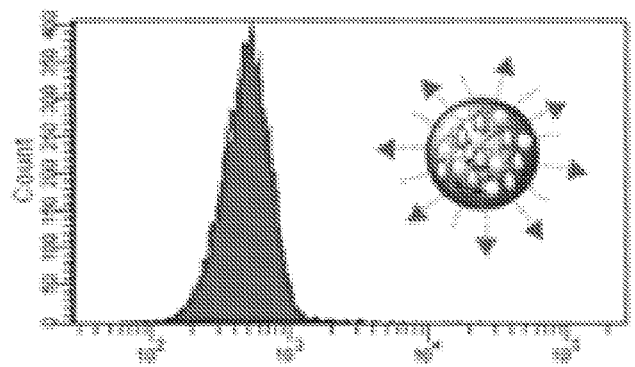

The targeting capabilities of the PSMA-targeted nanoparticles were tested in vitro. In these experiments, 2.5% of the fluorescent probe PLGA-Alexa 488 was added to the organic stream containing the polymers. This amount of PLGA-Alexa 488 does not affect the nanoparticle physicochemical properties, but is high enough to be detected readily by fluorescence assisted cell sorting (FACS) at very low concentrations of nanoparticles. To test the targeting capabilities of the nanoparticles, the nanoparticles were incubated with PSMA-overexpressing LNCaP cells for 4 hours. The cells were then treated them with trypsin, and the fluorescence intensity of 10,000 cells was assessed using FACS (FIG. 9). The cells treated with PSMA-targeted nanoparticles had 8-times more fluorescence than cells treated with non-targeted nanoparticles. FACS histograms of fluorescence versus counts show that nanoparticle uptake by cells occurred uniformly (e.g., all or a majority or cells engulfing the nanoparticles) rather than unevenly (e.g., few cells engulfing most of the nanoparticles) (FIG. 10). These results indicate that the dual-drug targeted nanoparticles are capable of selectively targeting cells over-expressing PSMA receptors, and that they can enter the cells more readily than non-targeted nanoparticles.

Figure 11:
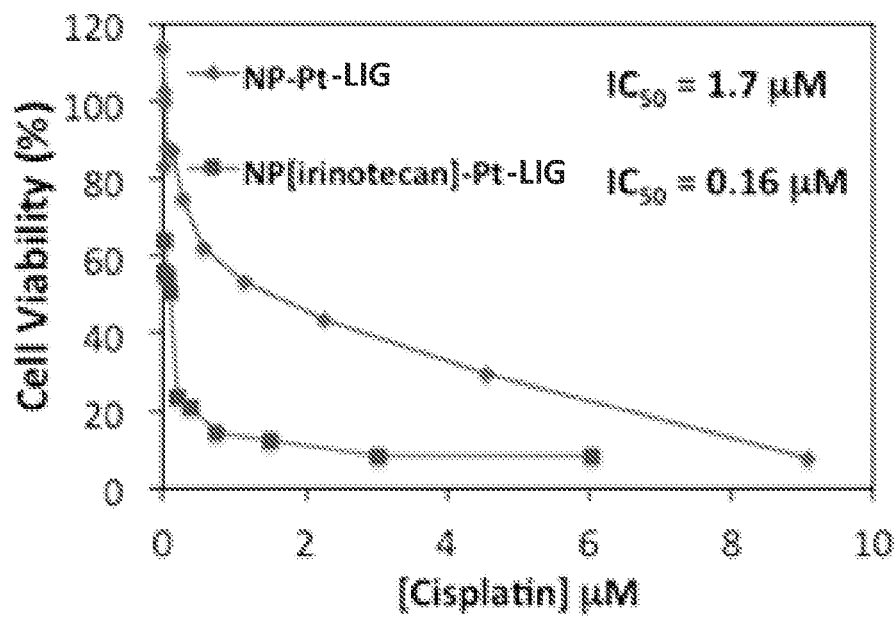
FIG. 11 is a graph showing the percentage cell viability in LNCaP cells following treatment with PMSA-targeted cisplatin-containing nanoparticles (NP-Pt-LIG) and PMSA-targeted irinotecan- and cisplatin-containing nanoparticles (NP-irinotecan-Pt-LIG).
Figure 12:
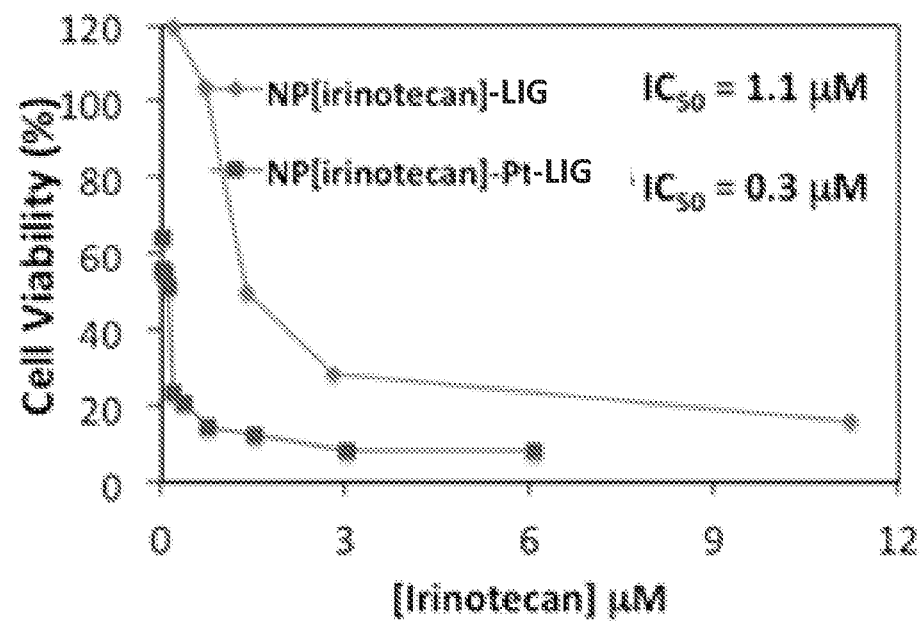
FIG. 12 is a graph showing the percentage cell viability in LNCaP cells following treatment with PMSA-targeted irinotecan nanoparticles (NP-irinotecan-LIG) and PMSA-targeted irinotecan- and cisplatin-containing nanoparticles (NP-irinotecan-Pt-LIG).
Figures 13, 14:
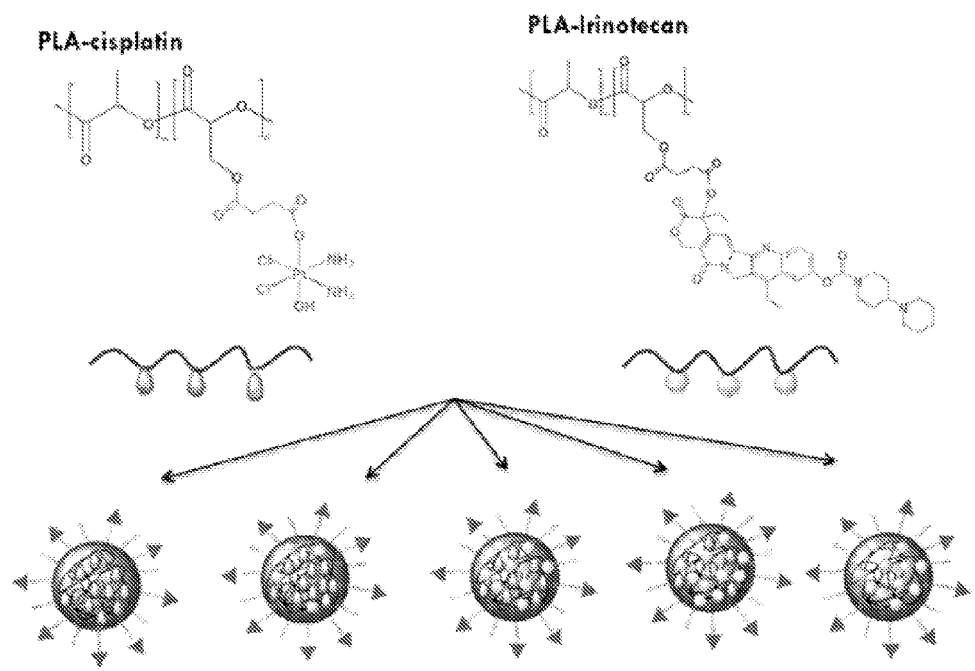
FIG. 13 is table showing the combination index calculated for the PMSA-targeted irinotecan- and cisplatin-containing nanoparticles (irinotecan-cisplatin NPs). The combination index was calculated by the Talay and Chou method at $ED_{80}$. According to the metric 0.20 represents strong synergy.
FIG. 14 is a schematic diagram showing the synthesis of nanoparticles containing both PLA-cisplatin, PLA-irinotecan. PLGA-PEG-LIG, and PLGA-PEG.

Cytotoxicity studies were performed in vitro to assess the relative ability of the cisplatin- and irinotecan-containing nanoparticles to induce LNCaP cell death. To do this, targeted nanoparticles loaded with irinotecan (NP-IRN), with cisplatin (NP-Pt), or both (NP-IRN-Pt) were exposed to LNCaP cells at different concentrations, and cytotoxicity was evaluated using a MTT assay. Based on the concentration of drugs in present in each nanoparticle, dose-response curves and the $IC_{50}$ values for each nanoparticle formulation were generated (FIGS. 11 and 12). NP-IRN-Pt was 3.6-fold and 10.6-fold more toxic than NP-Pt and NP-IRN, respectively. While these data suggest NP-IRN-Pt is more cytotoxic than the single-drug nanoparticles, it does not assess whether this was a synergistic or simply an additive effect. The Talay and Chou method (Chou et al., *Pharmacol. Res.* 58:621-681, 2006) was used to calculate the combination index (CI) at ED80 of NP-IRN-Pt, as previously reported by others for a similar system (Tardi et al., *Mol. Cancer Ther.* 8:2266-2275, 2009). The CI indicates the synergism of the dual-drug nanoparticles. For example, a CI~1 indicates an additive effect, CI>1 indicates an antagonistic effect, and CI<1 indicates a synergistic effect. NP-IRN-Pt was determined to have a remarkable CI of 0.20, which falls in the range of strong synergism (Chou et al., *Pharmacol. Res.* 58:621-681, 2006) (FIG. 13). These data demonstrate that the PSMA-targeted NP-IRN-Pt exhibits synergistic cytotoxicity against prostate cancer cells.

Figure 15:
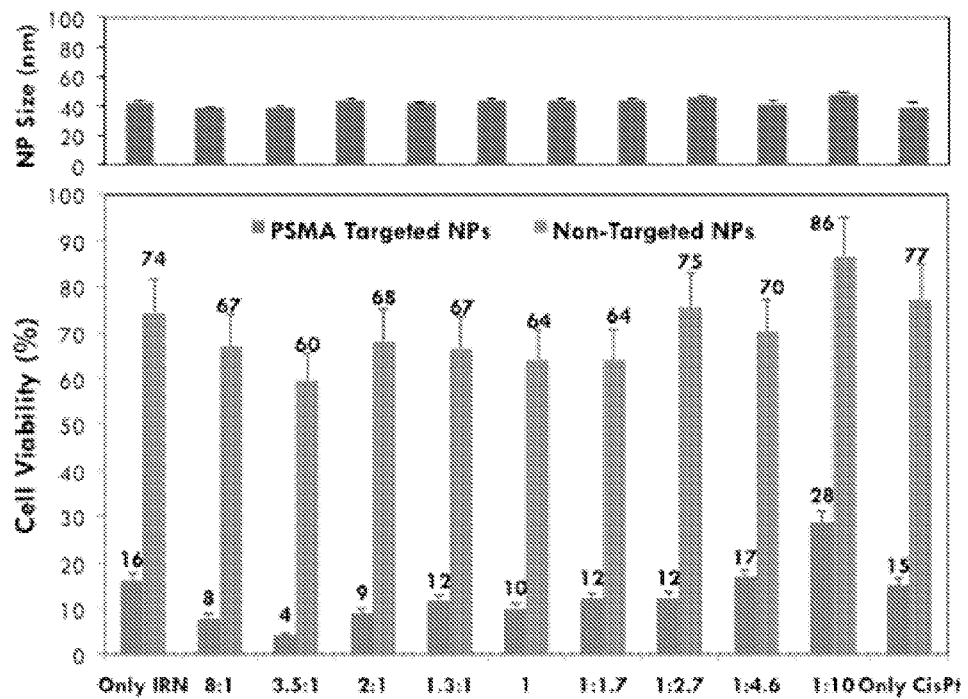
FIG. 15 is a set of two graphs showing the average size (top graph) and percent cell viability of human prostatic carcinoma (LNCaP) cells following treatment with 1 mg/mL for 12 hours (bottom graph) of nanoparticles containing PLA-cisplatin, PLA-irinotecan, PLGA-PEG-LIG, and PGLA-PEG and having different ratios of irinotecan to cisplatin, and recovery in fresh culture medium for 48 hours.

Example 2. PMSA-Targeted Nanoparticles Containing Conjugated Irinotecan and Use of these Nanoparticles to Mediate Prostate Cancer Cell Death Using the methods generally described in Example 1, nanoparticles were formed that contain PLGA-PEG-LIG, PLGA-PEG, PLA-cisplatin, and PLA-irinotecan. The average size and the ability of these nanoparticles to induce cell death in a human prostate cancer cell line were assessed.
Materials
 Polymers The synthesis of PLA-irinotecan was accomplished by first synthesizing a PLA-OBn via a ring opening polymerization reaction, where a toluene-functionalized cyclic lactide monomer and simple lactide monomer were dissolved in a toluene solution containing benzyl alcohol (initiator) and Tin catalyst. The resulting solution was refluxed at 120° C. for 10 hours. Then, the hydroxyl functionalized biodegradable polylactide polymer (PLA-OH) was obtained by benzyl deprotection using a Pd/C catalyst at 50 psi pressure for 8 hours. From this polymer, the carboxylic acid group functionalized polylactide polymer (PLA-COOH) was achieved by reacting the PLA-OH polymer with an excess of succinic anhydride in the presence of base for 48 hours in dichloromethane. Finally, conjugation of the irinotecan to PLA polymer was accomplished by an ester coupling reaction between PLA-COOH polymer with irinotecan via N,N'-dichlorohexylcarboimide/hydroxybenzotriazole. PLGA-PEG-LIG, PLGA-PEG, and PLA-cisplatin were obtained or synthesized as described in Example 1.
 Synthesis of Targeted and Non-Targeted Nanoparticles For the generation of the targeted nanoparticles, PLA-cisplatin and PLA-irinotean were premixed in acetonitrile at different ratios together with PLGA-PEG-LIG and unmodified PLGA-PEG to yield a polymer precursor solution of 10 mg/mL. A schematic of the generation of these nanoparticles is depicted in FIG. 14. For the generation of the non-targeted nanoparticles, PLA-cisplatin, PLA-irinotecan, and PLGA-PEG were mixed to yield a polymer precursor solution of 10 mg/mL. The resulting precursor polymer mixture (for both the targeted and non-targeted nanoparticles) was then mixed with acetonitrile in microfluidic channels at a ratio of 1:10 (acetonitrile:water) to yield nanoparticles. The cisplatin:irinotecan drug ratios in the resulting nanoparticles were altered by mixing different ratios of PLA-cisplatin and PLA-irinotecan in the precursor polymer mixture, while keeping the total concentration of polymers present in the precursor polymer mixture fixed. In this fashion, twenty-two different nanoparticle formulations were generated. Targeted and non-targeted nanoparticles were generated having one of the following ratios of irinotecan to cisplatin: 8:1, 3.5:1, 2:1, 1.3:1, 1, 1:1.7, 1:2.7, 1:4.6, and 1:10. Control nanoparticles were generated that contain only irinotecan and only cisplatin.
Results Targeted and non-targeted nanoparticles containing irinotecan covalently linked to a polymer and containing different ratios of irinotecan to cisplatin were generated. The average size of the resulting nanoparticles was determined as described in Example 1. The resulting data show that the size of the nanoparticles remained consistent despite variation in the ratio of irinotecan to cisplatin (FIG. 15, top panel). The ability of the targeted and non-targeted nanoparticles containing conjugated irinotecan to induce cell death in human prostate cancer cells was also determined (e.g., performed using the MTT assay described in Example 1). The resulting data show that the PSMA-targeted nanoparticles are more effective in inducing human prostate cancer cell death and that PMSA-targeted nanoparticles containing a irinotecan to cisplatin ratio of 3.5:1 had the highest cytotoxic effect on human prostate cancer cells (FIG. 15, bottom panel).

In sum, these data indicate that targeted and non-targeted nanoparticles containing conjugated irinotecan and conjugated cisplatin can be formed, and that these nanoparticles have a strong cytotoxic effect on human prostate cancer cell lines (at a level that is greater than the cytotoxic effect achieved by similar nanoparticles containing conjugated irinotecan alone or nanoparticles containing conjugated cisplatin alone). These data further show that nanoparticles containing specific ratios of conjugated irinotecan and conjugated cisplatin have a significantly and unexpectedly improved cytotoxic effect on human prostate cancer cells.

Example 3. PLA and PLGA-PEG Nanoparticle Tolerance

A combination of PLA-OH and PLGA-PEG polymers (described in Example 1) were mixed at a molar ratio of 1:1 to generate five different compositions. The nanoparticles in each of the five different compositions were generated using a different total concentration of polymers. Each of the five nanoparticle compositions were administered by tail vein injection (intravenously) once at day 0 to healthy 5- to 6-week old Swiss albino mice having a weight of around 21.9 grams to 25.0 grams, and the viability and weight of each mouse was monitored each day up to a total of 8 days. The nanoparticles present in the compositions were generated using the methods generally described herein. The administered compositions were generated by suspending the nanoparticles in saline. The total dose of polymers administered to mice was 87 mg/kg (1 mouse), 174 mg/kg (2 mice), 870 mg/kg (3 mice), 1740 mg/kg (2 mice), and 4360 mg/kg (3 mice).

Figure 16:
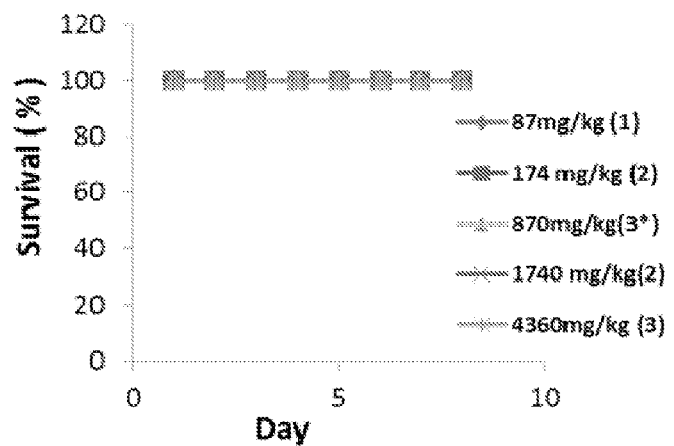
FIG. 16 is a graph showing the survival rate of Swiss albino mice over time following intravenous administration (at day 0) of nanoparticles containing different concentrations of PLA-OH polymer blended in a 1:1 ratio with PLGA-PEG polymer. The total dose of polymers administered to mice was 87 mg/kg (1 mouse), 174 mg/kg (2 mice), 870 mg/kg (3 mice), 1740 mg/kg (2 mice), and 4360 mg/kg (3 mice).
Figure 17:
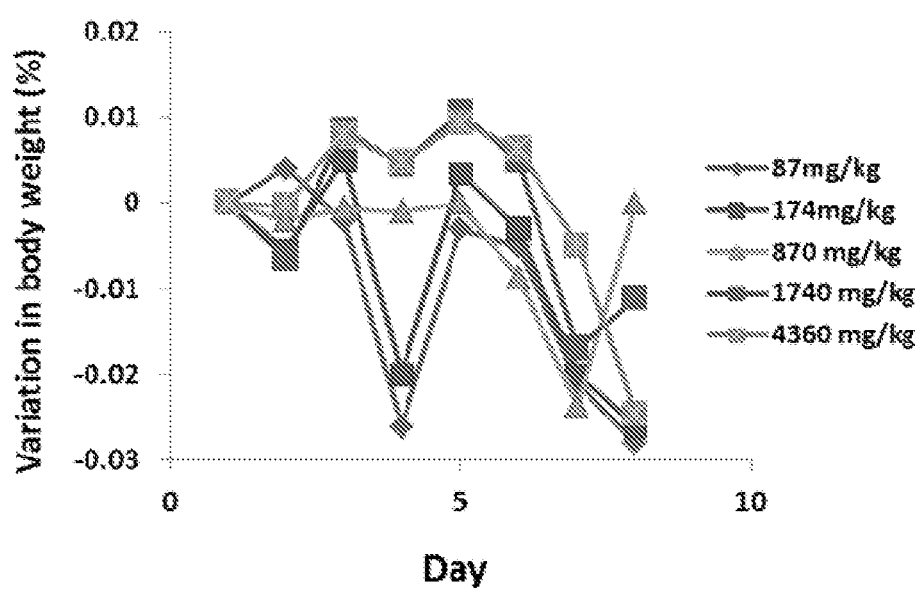
FIG. 17 is a graph showing the percentage change in body weight in mice over time following intravenous administration (at day 0) of nanoparticles containing different concentrations of PLA-OH polymer blended in a 1:1 ratio with PLGA-PEG polymer. The total dose of polymers administered to mice was 87 mg/kg (1 mouse), 174 mg/kg (2 mice), 870 mg/kg (3 mice), 1740 mg/kg (2 mice), and 4360 mg/kg (3 mice).

The results of these experiments are shown in FIGS. 16 and 17. These data show that the nanoparticles described herein are well tolerated in mice at doses above 4 g/kg.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:
1. A composition comprising a nanoparticle, the nanoparticle comprising:
 a plurality of polymers comprising
  (i) at least one amphiphilic polymer comprising at least one first hydrophobic polymer and at least one hydrophilic polymer, and
  (ii) at least one second hydrophobic polymer that is biodegradable and is linked to one or more platinum (Pt)-containing chemotherapeutic agents, wherein the chemotherapeutic agents are linked to one or more pendant functional groups present along a length of the second hydrophobic polymer; and a topoisomerase inhibitor selected from the group consisting of irinotecan, SN-38, topotecan, and camptothecin;
wherein the one or more Pt-containing chemotherapeutic agents are all cisplatin;
wherein the polymers self-assemble in an aqueous liquid to form the nanoparticle, wherein the at least one first hydrophobic polymer and the at least one second hydrophobic polymer form a hydrophobic core of the nanoparticle and the at least one hydrophilic polymer forms a shell of the nanoparticle, wherein the Pt-containing chemotherapeutic agent and the topoisomerase inhibitor are present within the hydrophobic core of the nanoparticle in a synergistic ratio between about 1:4 to about 4:1, and
wherein the polymers are formulated to provide a time-dependent, condition-dependent, or both time-dependent and condition-dependent controlled release of the one or more Pt-containing chemotherapeutic agents and the topoisomerase inhibitor from the nanoparticle.

2. The composition of claim 1, further comprising a targeting moiety linked to at least one of the polymers, wherein the targeting moiety is exposed on an outer surface of the nanoparticle.

3. The composition of claim 1, wherein the topoisomerase inhibitor is linked to at least one of the polymers.

4. The composition of claim 2, wherein the targeting moiety is linked to at least one of the polymers through an ester, an amide, or an ether bond.

5. The composition of claim 1, wherein the plurality of polymers includes at least one amphiphilic polymer.

6. The composition of claim 1, wherein the Pt-containing chemotherapeutic agent is linked to the hydrophobic polymer through an ester, an amide, or an ether bond.

7. The composition of claim 1, wherein the nanoparticle further comprises an outer layer comprising a surfactant.

8. The composition of claim 2, wherein:
the plurality of polymers comprises poly(lactide-co-glycolic acid)-polyethylene glycol (PLGA-PEG) and polylactic acid;
the targeting moiety is S,S-2[3-][5-amino-1-carboxypentyl]-ureido]-pentanedioic acid (LIG); and
the topoisomerase inhibitor is irinotecan.

9. The composition of claim 1, wherein the nanoparticle has a diameter of about 40 nm to 80 nm.

10. The composition of claim 1, further comprising one or more additional anti-cancer agents selected from the group consisting of: an alkylating agent, an antimetabolite, an anthracycline, a plant alkyloid, and a therapeutic antibody or antigen-binding antibody fragment that specifically binds to a tumor antigen.

11. A pharmaceutical composition comprising the composition of claim 1.

12. A method of reducing the proliferation of a cancer cell, the method comprising contacting a cancer cell with an amount of the composition of claim 1 sufficient to reduce the proliferation of the cancer cell.

13. A method of making a nanoparticle according to claim 1, the method comprising:
mixing (i) a plurality of polymers, wherein at least a fraction of the polymers comprise a hydrophobic polymer linked to a platinum (Pt)-containing chemotherapeutic agent; and (ii) a topoisomerase inhibitor in an organic solvent to form an organic precursor solution; and contacting the organic precursor solution with an aqueous solvent to achieve a ratio of 5:1 to 20:1 volume of organic precursor solution to volume of aqueous solvent, wherein the contacting results in the self-assembly of a nanoparticle.

14. The method of claim 13, wherein the plurality of polymers further comprises at least one polymer linked to a targeting moiety.

15. The method of claim 13, wherein the topoisomerase inhibitor is linked to at least one of the polymers.

16. The method of claim 14, wherein:
the plurality of copolymers comprises poly (lactide-co-glycolic acid) polyethylene glycol (PLGA-PEG) and polylactic acid (PLA);
the targeting moiety is S,S-2[3-][5-amino-1-carboxypentyl]-ureido]-pentanedioic acid (LIG);
the Pt-containing chemotherapeutic agent is cisplatin; and
the topoisomerase inhibitor is irinotecan.

17. A composition comprising a nanoparticle, the nanoparticle comprising:
a plurality of polymers comprising
(i) at least one amphiphilic polymer comprising at least one first hydrophobic polymer and at least one hydrophilic polymer, and
(ii) at least one second hydrophobic polymer that is biodegradable and is linked to one or more topoisomerase inhibitors and to one or more platinum (Pt)-containing chemotherapeutic agents, wherein the Pt-containing chemotherapeutic agents and topoisomerase inhibitors are linked to one or more pendant functional groups present along a length of the biodegradable hydrophobic polymer; wherein the polymers self-assemble in an aqueous liquid to form the nanoparticle, wherein the at least one first hydrophobic polymer and the at least one second hydrophobic polymer form a hydrophobic core of the nanoparticle and the at least one hydrophilic polymer forms a shell of the nanoparticle,
wherein the one or more Pt-containing chemotherapeutic agents are all cisplatin;
wherein the topoisomerase inhibitor is selected from the group consisting of irinotecan, SN-38, topotecan, and camptothecin;
wherein the Pt-containing chemotherapeutic agent and the topoisomerase inhibitor are present within the hydrophobic core of the nanoparticle in a synergistic ratio between about 1:4 to about 4:1, and
wherein the polymers are formulated to provide a time-dependent, condition-dependent, or both time-dependent and condition-dependent controlled release of the one or more Pt-containing chemotherapeutic agents and the topoisomerase inhibitor from the nanoparticle.

18. The composition of claim 1, wherein the pendant functional groups of the hydrophobic polymer comprise any one or more of hydroxyl, carboxyl, amine, amide, carbamate, maleimide, thiol, halide, azide, proparzyl, or allyl functional groups.

19. The composition of claim 17, wherein the pendant functional groups of the hydrophobic polymer comprise any one or more of hydroxyl, carboxyl, amine, amide, carbamate, maleimide, thiol, halide, azide, proparzyl, or allyl functional groups.

20. The composition of claim 1, wherein the hydrophobic polymer comprises approximately one pendant functional group for every 1, 2, 3, 4, 5, 6, 7, 8, 9, 10, 12, 15, or 20 monomer units.

21. The composition of claim 17, wherein the hydrophobic polymer comprises approximately one pendant functional group for every 1, 2, 3, 4, 5, 6, 7, 8, 9, 10, 12, 15, or 20 monomer units.

22. The composition of claim 1, wherein the first hydrophobic polymer is also biodegradable and wherein the (Pt)-containing chemotherapeutic agents are also linked to one or more pendant functional groups present along a length of the first hydrophobic polymer.

23. The composition of claim 17, wherein the first hydrophobic polymer is also biodegradable and wherein the (Pt)-containing chemotherapeutic agents and topoisomerase inhibitors are also linked to one or more pendant functional groups present along a length of the first hydrophobic polymer.

* * * * *

UNITED STATES PATENT AND TRADEMARK OFFICE
CERTIFICATE OF CORRECTION

PATENT NO. : 9,931,410 B2
APPLICATION NO. : 14/434300
DATED : April 3, 2018
INVENTOR(S) : Pedro M. Valencia et al.

Page 1 of 1

It is certified that error appears in the above-identified patent and that said Letters Patent is hereby corrected as shown below:

In the Claims

In Column 41, Line 51, Claim 10, delete "alkyloid," and insert -- alkaloid, --

In Column 42, Line 57, Claim 18, delete "proparzyl" and insert -- propargyl, --

In Column 42, Line 62, Claim 19, delete "proparzyl" and insert -- propargyl, --

Signed and Sealed this
Sixth Day of November, 2018

Andrei Iancu
*Director of the United States Patent and Trademark Office*